United States Patent
Watanabe et al.

(10) Patent No.: US 11,518,889 B2
(45) Date of Patent: Dec. 6, 2022

(54) MODIFIED GRAPHENE, METHOD OF PRODUCING MODIFIED GRAPHENE, MODIFIED GRAPHENE-RESIN COMPOSITE, MODIFIED GRAPHENE SHEET, AND MODIFIED GRAPHENE DISPERSION

(71) Applicant: CANON KABUSHIKI KAISHA, Tokyo (JP)

(72) Inventors: Taiki Watanabe, Akishima (JP); Akiko Kitao, Kawasaki (JP); Koichi Suzuki, Yokohama (JP); Yuma Kobayashi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 290 days.

(21) Appl. No.: 16/793,557

(22) Filed: Feb. 18, 2020

(65) Prior Publication Data

US 2020/0270463 A1 Aug. 27, 2020

(30) Foreign Application Priority Data

Feb. 27, 2019 (JP) .............................. JP2019-034911
Feb. 27, 2019 (JP) .............................. JP2019-034913
Feb. 12, 2020 (JP) .............................. JP2020-021921

(51) Int. Cl.
*C09C 1/44* (2006.01)
*C08K 9/06* (2006.01)
(Continued)

(52) U.S. Cl.
CPC ................ *C09C 1/44* (2013.01); *C07C 15/08* (2013.01); *C07C 15/085* (2013.01); *C07C 25/13* (2013.01);
(Continued)

(58) Field of Classification Search
None
See application file for complete search history.

(56) References Cited

U.S. PATENT DOCUMENTS 9,371,462 B2 6/2016 Watanabe et al.
9,458,323 B2 10/2016 Higashi et al.
(Continued)

FOREIGN PATENT DOCUMENTS

JP     3980637 B2    9/2007
JP     5098064 B1    12/2012
(Continued)

OTHER PUBLICATIONS

Gabriel Gever, "Hydrazinoalkanols," 76 J. Am. Chem. Soc. 1283-1285 (Mar. 1954).

*Primary Examiner* — William D Young
(74) *Attorney, Agent, or Firm* — Venable LLP

(57) ABSTRACT

The modified graphene includes a structure represented by the following formula (I), wherein the modified graphene has a ratio (g/d) of an intensity "g" of a G band to an intensity "d" of a D band of 1.0 or more in a Raman spectroscopy spectrum thereof:

$$\text{Gr1-Ar1-X1-(Y1)}_{n1} \quad\quad\quad (I)$$

in the formula (I), Gr1 represents a single-layer graphene or a multilayer graphene, Ar1 represents an arylene group having 6 to 18 carbon atoms, X1 represents a single bond, a linear, branched, or cyclic alkylene group having 1 to 20 carbon atoms, or a group obtained by substituting at least one carbon atom in a linear, branched, or cyclic alkylene group having 1 to 20 carbon atoms with at least one structure selected from the group consisting of —O—, —NH—,
(Continued)

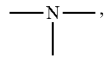

—CO—, —COO—, —CONH—, and an arylene group.

12 Claims, 3 Drawing Sheets

(51) Int. Cl.
*C08K 3/04* (2006.01)
*C09D 5/24* (2006.01)
*C09D 7/62* (2018.01)
*C07C 15/085* (2006.01)
*C07C 15/08* (2006.01)
*C07C 25/13* (2006.01)
*C07C 255/50* (2006.01)
*C07C 205/06* (2006.01)
*C07C 49/78* (2006.01)
*C07C 233/65* (2006.01)
*C07C 233/78* (2006.01)
*C07C 63/16* (2006.01)
*C07F 9/38* (2006.01)
*C08G 77/42* (2006.01)

(52) U.S. Cl.
CPC .............. *C07C 49/78* (2013.01); *C07C 63/16* (2013.01); *C07C 205/06* (2013.01); *C07C 233/65* (2013.01); *C07C 233/78* (2013.01); *C07C 255/50* (2013.01); *C07F 9/3834* (2013.01); *C08G 77/42* (2013.01); *C08K 3/042* (2017.05); *C08K 9/06* (2013.01); *C09D 5/24* (2013.01); *C09D 7/62* (2018.01); *C01P 2006/22* (2013.01); *C01P 2006/40* (2013.01); *C08K 2201/001* (2013.01); *C08K 2201/011* (2013.01)

(56) References Cited

U.S. PATENT DOCUMENTS

| | | | |
|---|---|---|---|
| 2010/0206363 A1* | 8/2010 | Choi | H05B 33/28 428/408 |
| 2011/0052813 A1* | 3/2011 | Ho | B82Y 30/00 427/256 |
| 2011/0059871 A1* | 3/2011 | Tour | C09K 8/035 507/140 |
| 2016/0002047 A1 | 1/2016 | Virtanen | |
| 2017/0107787 A1* | 4/2017 | Tour | C08K 3/042 |

FOREIGN PATENT DOCUMENTS

| | | |
|---|---|---|
| JP | 2013-079176 A | 5/2013 |
| JP | 2016-27092 A | 2/2016 |
| JP | 2016-27093 A | 2/2016 |
| JP | 2017-154928 A | 9/2017 |
| WO | 96/18690 A1 | 6/1996 |

* cited by examiner

MODIFIED GRAPHENE, METHOD OF PRODUCING MODIFIED GRAPHENE, MODIFIED GRAPHENE-RESIN COMPOSITE, MODIFIED GRAPHENE SHEET, AND MODIFIED GRAPHENE DISPERSION

BACKGROUND OF THE INVENTION

Field of the Invention

The present disclosure relates to a modified graphene, a method of producing a modified graphene, a modified graphene-resin composite, a modified graphene sheet, and a modified graphene dispersion.

Description of the Related Art

Carbon materials, such as a graphene, graphite, and a carbon nanotube, each have excellent electrical, thermal, optical, and mechanical characteristics, and hence the materials have been expected to find a wide variety of applications in fields including a battery material, an energy-storing material, an electronic device, and a composite material. When the characteristics of such various carbon materials are caused to effectively function and are industrially utilized, the control of the cohesive force of each of the carbon materials to improve the dispersibility thereof in a dispersion medium may be required.

A production method including subjecting the surface of a carbon material to a chemical treatment to introduce a substituent so that the surface may be modified has been known as an approach to suppressing the cohesive force of the material.

In Japanese Patent No. 5098064, there is a description of a method of producing a graphene oxide obtained through the introduction of an oxygen-containing group into the surface of a graphene by Hummers' method including using graphite and an oxidant. In addition, in Japanese Patent No. 3980637, there is a disclosure of a method of producing graphene powder having an amino group (—NH$_2$), the method including causing graphite powder and a treatment agent having an amino group, such as a monodiazonium salt of p-phenylenediamine, to react with each other in water.

SUMMARY OF THE INVENTION

One aspect of the present disclosure is directed to providing a modified graphene improved in dispersibility in a dispersion medium without the impairment of excellent electroconductivity and excellent thermal conductivity inherent in a graphene.

Another aspect of the present disclosure is directed to providing a method of producing a modified graphene excellent in dispersibility in a dispersion medium without the impairment of excellent electroconductivity and excellent thermal conductivity inherent in a graphene.

In addition, another aspect of the present disclosure is directed to providing a modified graphene-resin composite, a modified graphene sheet, and a modified graphene dispersion each having excellent electroconductivity and excellent thermal conductivity.

According to one aspect of the present disclosure, there is provided a modified graphene having a structure represented by the following formula (I), wherein the modified graphene has a ratio (g/d) of an intensity "g" of a G band to an intensity "d" of a D band of 1.0 or more in a Raman spectroscopy spectrum thereof:

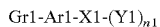     (I)

in the formula (I), Gr1 represents a single-layer graphene or a multilayer graphene, Ar1 represents an arylene group having 6 to 18 carbon atoms, X1 represents any one selected from a single bond, a linear, branched, or cyclic alkylene group having 1 to 20 carbon atoms, and a group obtained by substituting at least one carbon atom in a linear, branched, or cyclic alkylene group having 1 to 20 carbon atoms with at least one structure selected from the group consisting of —O—, —NH—,

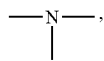

—CO—, —COO—, —CONH—, and an arylene group, Y1 represents, when the X1 represents a single bond, an atom or a group bonded to at least one carbon atom in the Ar1, when the X1 represents a linear, branched, or cyclic alkylene group having 1 to 20 carbon atoms, an atom or a group bonded to a carbon atom in the alkylene group, or when the X1 represents a group obtained by substituting at least one carbon atom in a linear, branched, or cyclic alkylene group having 1 to 20 carbon atoms with at least one structure selected from the group consisting of —O—, —NH—,

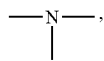

—CO—, —COO—, —CONH—, and an arylene group, an atom or a group bonded to a carbon atom in the group, and the Y1 represents at least one atom or group selected from the group consisting of a hydrogen atom, a fluorine atom, a chlorine atom, a bromine atom, and an iodine atom, a fluoroalkyl group having 1 to 6 carbon atoms, a cyano group, a nitro group, an acyl group, an amide group, a vinyl group, a carboxylic acid group, a carboxylic acid ester group, and a phosphoric acid group, an alkylsilyl group having 3 to 6 carbon atoms, an alkylsilyl ether group having 3 to 6 carbon atoms, and a siloxane group, and n1 represents an integer of 1 or more, and when the n1 represents 2 or more, the Y1s may represent groups identical to each other or groups different from each other.

According to another aspect of the present disclosure, there is also provided a method of producing a modified graphene including a step of bonding a group represented by A1 in the following formula (V) to a carbon atom of a surface of a graphene through a radical addition reaction based on abstraction of a hydrogen atom from a compound represented by the following formula (V) in an aqueous system:

     (V)

in the formula (V), A1 represents a group represented by —Ar1-X1-(Y1)$_{n1}$, Ar1 represents an arylene group having 6 to 18 carbon atoms, X1 represents any one selected from a single bond, a linear, branched, or cyclic alkylene group having 1 to 20 carbon atoms, and a group obtained by substituting at least one carbon atom in a linear, branched or cyclic alkylene group having 1 to 20 carbon atoms with at least one structure selected from the group consisting of —O—, —NH—,

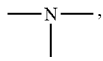

—CO—, —COO—, —CONH—, and an arylene group, Y1 represents, when the X1 represents a single bond, an atom or a group bonded to at least one carbon atom in the Ar1, or when the X1 does not represent a single bond, an atom or a group bonded to a carbon atom of the X1, and the Y1 represents at least one atom or group selected from the group consisting of a hydrogen atom, a fluorine atom, a chlorine atom, a bromine atom, and an iodine atom, a fluoroalkyl group having 1 to 6 carbon atoms, a cyano group, a nitro group, an acyl group, an amide group, a vinyl group, a carboxylic acid group, a carboxylic acid ester group, and a phosphoric acid group, an alkylsilyl group having 3 to 6 carbon atoms, an alkylsilyl ether group having 3 to 6 carbon atoms, and a siloxane group, and n1 represents an integer of 1 or more, and when the n1 represents 2 or more, the Y1s may represent groups identical to each other or groups different from each other.

According to another aspect of the present disclosure, there is also provided a method of producing a modified graphene including causing at least one kind of treatment agent selected from a compound represented by the following formula (IX) and a compound represented by the following formula (X) to react with a graphene to chemically bond a group represented by A1 in the formula to a carbon atom of a surface of the graphene:

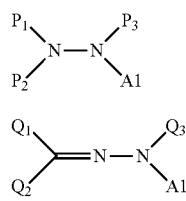

in the formula (IX), $P_1$, $P_2$, and $P_3$ each independently represent a hydrogen atom, an alkyl group, an aryl group, a carboxylic acid ester group, or —S(=O)$_2$—R', and not all of the $P_1$, the $P_2$, and the $P_3$ simultaneously represent hydrogen atoms, R' represents a hydroxy group, an alkyl group, or an aryl group, and A1 represents a group represented by —Ar1-X1-(Y1)$_{n1}$, and in the formula (X), $Q_1$ and $Q_2$ each independently represent a hydrogen atom, an alkyl group, an aryl group, a halogen atom, a cyano group, a nitro group, an amino group, an alkoxy group, a thioalkoxy group, an acyl group, a carboxylic acid ester group, an aryloxy group, a carboxylic acid group, a sulfonic acid group, a phosphoric acid group, or a phosphonic acid group, and the $Q_1$ and the $Q_2$ do not simultaneously represent hydrogen atoms, $Q_3$ represents a hydrogen atom, an alkyl group, an aryl group, or a carboxylic acid ester group, and A1 represents a group represented by —Ar1-X1-(Y1)$_{n1}$, the Ar1 represents an arylene group having 6 to 18 carbon atoms, X1 represents a single bond, a linear, branched, or cyclic alkylene group having 1 to 20 carbon atoms, or a group obtained by substituting at least one carbon atom in a linear, branched or cyclic alkylene group having 1 to 20 carbon atoms with at least one structure selected from the group consisting of —O—, —NH—,

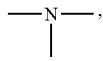

—CO—, —COO—, —CONH—, and an arylene group, Y1 represents, when the X1 represents a single bond, an atom or a group bonded to at least one carbon atom in the Ar1, when the X1 represents a linear, branched, or cyclic alkylene group having 1 to 20 carbon atoms, an atom or a group bonded to a carbon atom in the alkylene group, or when the X1 represents a group obtained by substituting at least one carbon atom in a linear, branched, or cyclic alkylene group having 1 to 20 carbon atoms with at least one structure selected from the group consisting of —O—, —NH—,

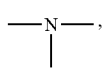

—CO—, —COO—, —CONH—, and an arylene group, an atom or a group bonded to a carbon atom in the group, and the Y1 represents at least one atom or group selected from the group consisting of a hydrogen atom, a fluorine atom, a chlorine atom, a bromine atom, and an iodine atom, a fluoroalkyl group having 1 to 6 carbon atoms, a cyano group, a nitro group, an acyl group, an amide group, a vinyl group, a carboxylic acid group, a carboxylic acid ester group, and a phosphoric acid group, an alkylsilyl group having 3 to 6 carbon atoms, an alkylsilyl ether group having 3 to 6 carbon atoms, and a siloxane group, and n1 represents an integer of 1 or more, and when the n1 represents 2 or more, the Y1s may represent groups identical to each other or groups different from each other.

According to one aspect of the present disclosure, there are provided a modified graphene-resin composite, a modified graphene sheet, and a modified graphene dispersion each including the modified graphene including the structure represented by the formula (I).

Further features of the present invention will become apparent from the following description of exemplary embodiments with reference to the attached drawings.

DESCRIPTION OF THE EMBODIMENTS

Figure 1:
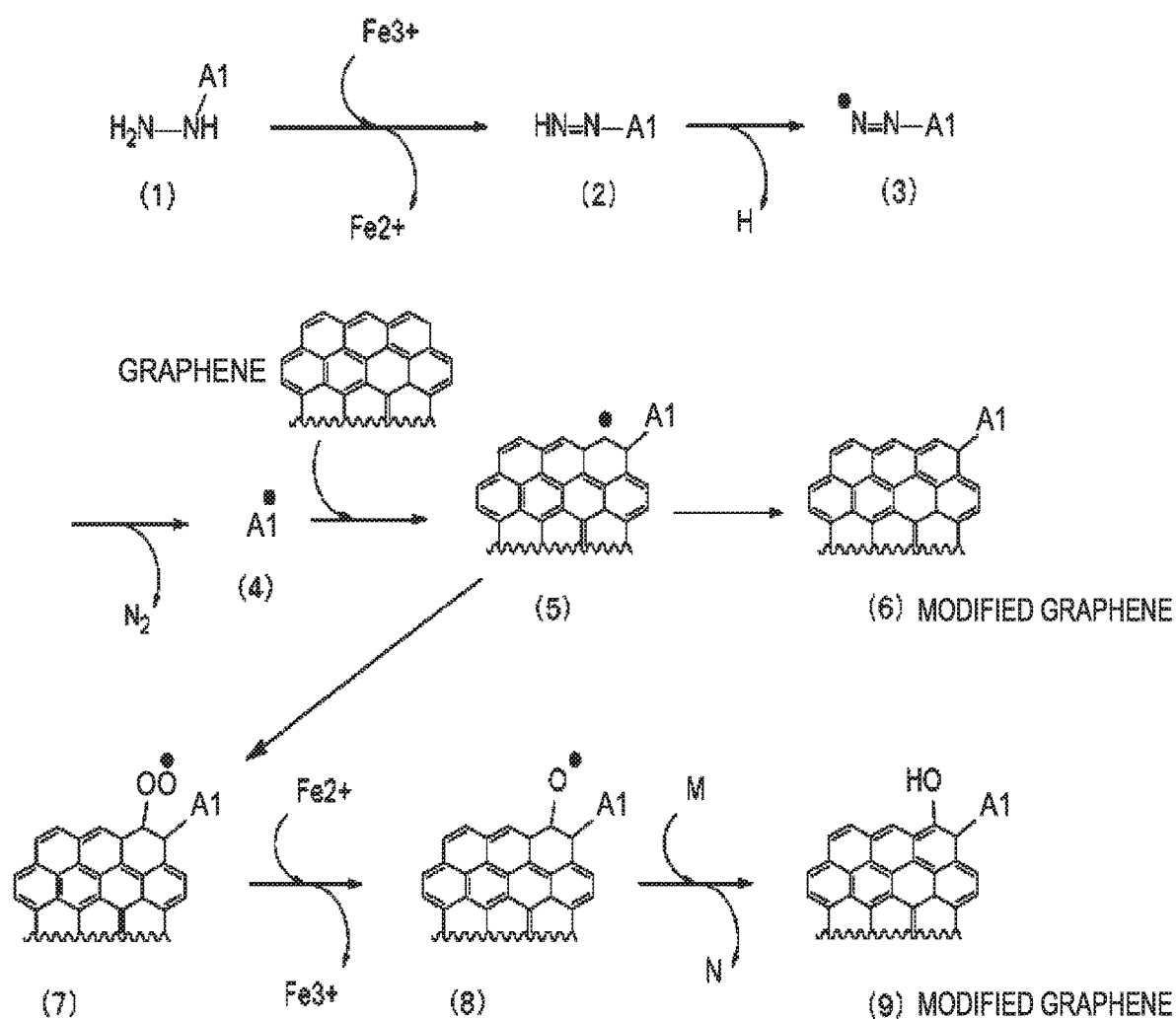
FIG. 1 is a view for illustrating assumed reaction mechanisms in obtaining a modified graphene in the case of using a compound represented by the formula (VI) according to one aspect of the present disclosure.

We have investigated the chemical modification of a graphene with a view to obtaining a graphene excellent in dispersibility in a dispersion medium without impairing high electroconductivity and high thermal conductivity inherent in the graphene.

The investigation has revealed that, in the method described in Japanese Patent No. 5098064, the functional group is introduced into the surface of the graphene together with the strong oxidant, and hence the graphene may be oxidized to break an $sp^2$ structure peculiar to the graphene. In addition, in the method described in Japanese Patent No. 3980637, a large amount of a radical may be generated in a short time period because the diazonium compound is liable to decompose, and hence radical generation cannot be controlled in a reaction system. It has been found that, as a result of the foregoing, the $sp^2$ structure peculiar to the graphene may be broken. When the $sp^2$ structure peculiar to the graphene is broken, excellent electroconductivity and excellent thermal conductivity inherent in the graphene may be impaired.

Meanwhile, Japanese Patent Application Laid-Open No. 2016-27092 and Japanese Patent Application Laid-Open No. 2016-27093 disclose a self-dispersible pigment and a method of producing thereof. However, Japanese Patent Application Laid-Open No. 2016-27092 and Japanese Patent Application Laid-Open No. 2016-27093 fail to teach or suggest the applicability of the method to a graphene.

Under such circumstances, we have made further investigations, and as a result, have found a modified graphene showing excellent dispersibility in a dispersion medium without impairing excellent characteristics inherent in a graphene, such as high electroconductivity and excellent thermal conductivity.

That is, a modified graphene according to one aspect of the present disclosure has a structure represented by the following formula (I), wherein the modified graphene has a ratio (g/d) of an intensity "g" of a G band to an intensity "d" of a D band of 1.0 or more in a Raman spectroscopy spectrum thereof.

$$\text{Gr1-Ar1-X1-(Y1)}_{n1} \quad \text{(I)}$$

Gr1, Ar1, X1, Y1, and n1 in the formula (I) are described. Gr1 represents a single-layer graphene or a multilayer graphene.
Ar1 represents an arylene group having 6 to 18 carbon atoms.
X1 represents a single bond, a linear, branched, or cyclic alkylene group having 1 to 20 carbon atoms, or a group obtained by substituting at least one carbon atom in a linear, branched, or cyclic alkylene group having 1 to 20 carbon atoms with at least one structure selected from the group consisting of —O—, —NH—,

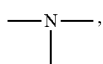

—CO—, —COO—, —CONH—, and an arylene group.
When the X1 represents a single bond, Y1 represents an atom or a group bonded to at least one carbon atom in the Ar1 (arylene group).

In addition, when the X1 represents a linear, branched, or cyclic alkylene group having 1 to 20 carbon atoms, the Y1 represents an atom or a group bonded to a carbon atom in the alkylene group.

Further, when the X1 represents a group obtained by substituting at least one carbon atom in a linear, branched, or cyclic alkylene group having 1 to 20 carbon atoms with at least one structure selected from the group consisting of —O—, —NH—,

—CO—, —COO—, —CONH—, and an arylene group, the Y1 represents an atom or a group bonded to a carbon atom in the group.

The Y1 represents at least one atom or group selected from the group consisting of a hydrogen atom, a fluorine atom, a chlorine atom, a bromine atom, and an iodine atom, a fluoroalkyl group having 1 to 6 carbon atoms, a cyano group, a nitro group, an acyl group, an amide group, a vinyl group, a carboxylic acid group, a carboxylic acid ester group, and a phosphoric acid group, an alkylsilyl group having 3 to 6 carbon atoms, an alkylsilyl ether group having 3 to 6 carbon atoms, and a siloxane group.

n1 represents an integer of 1 or more, and when the n1 represents 2 or more, the Y1s may represent groups identical to each other or groups different from each other.

The modified graphene according to the formula (I) can also be said to be such a graphene that —Ar1-X1-(Y1)$_{n1}$ is bonded as a modifying group to at least one of the carbon atoms forming the graphene.

In addition, the G band of the graphene in the Raman spectroscopy spectrum is one peak characteristic of the graphene, and is a peak that is derived from the in-plane motion of a carbon atom, and that appears at from around 1,580 cm$^{-1}$ to around 1,590 cm$^{-1}$. Meanwhile, the D band of the graphene in the Raman spectroscopy spectrum is a peak that results from a disturbance or a defect in the structure of the graphene, and that appears at around 1,350 cm$^{-1}$.

Even in an unmodified graphene, a disturbance or a defect is typically present in its structure. However, the ratio (g/d) of the intensity "g" of the G band of the unmodified graphene to the intensity "d" of the D band thereof does not become less than 1.0. In addition, the technical significance of the fact that the modified graphene according to one aspect of the present disclosure has a ratio (g/d) of 1.0 or more lies in that the number of disturbances or defects in the structure in the graphene does not increase even after the performance of its chemical modification.

Figure 3A:
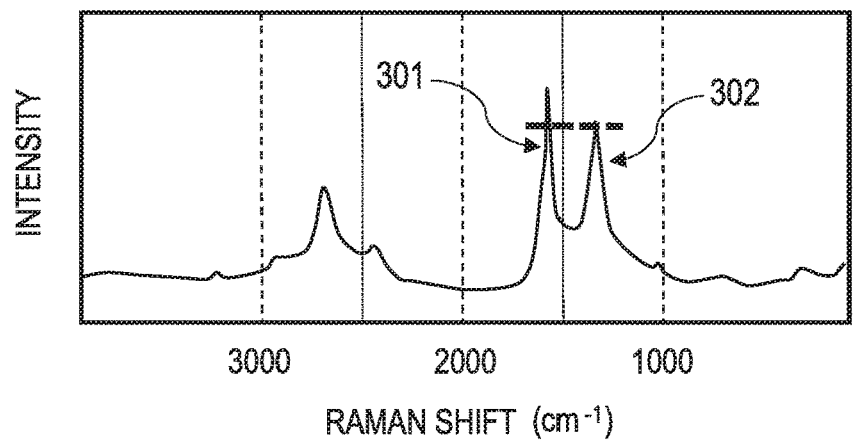
FIG. 3A is a chart of the Raman spectroscopy spectrum of a modified graphene according to one aspect of the present disclosure.
Figure 3B:
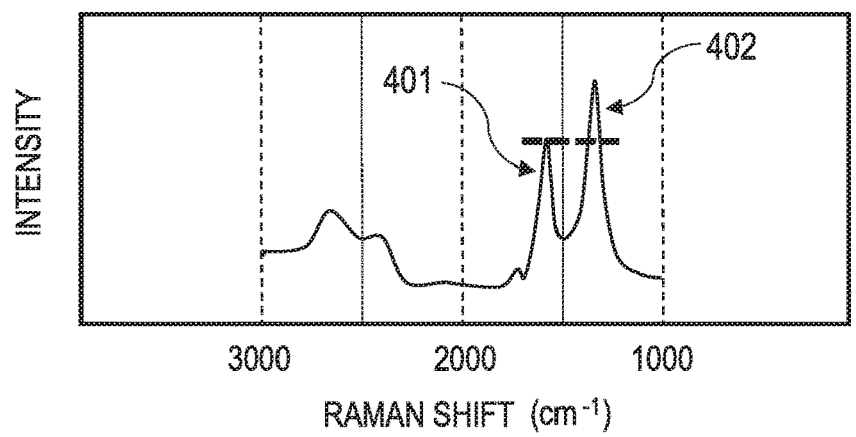
FIG. 3B is a chart of the Raman spectroscopy spectrum of a modified graphene having introduced thereinto a modifying group by Hummers' method involving using an oxidant.
Figure 3C:
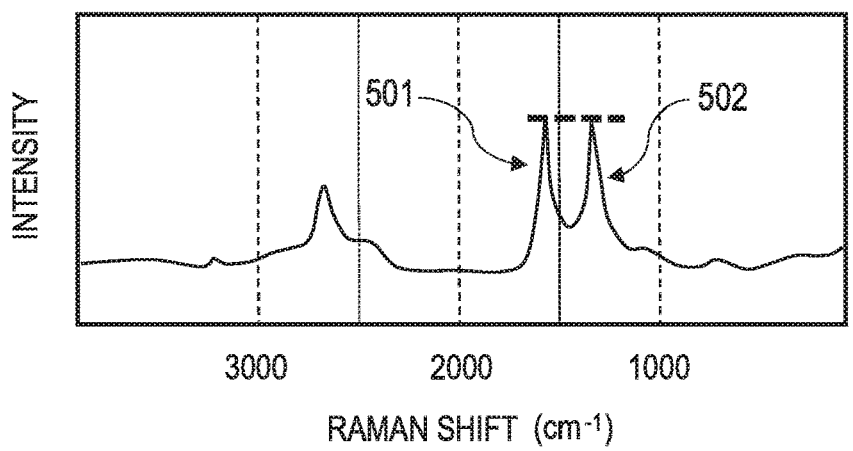
FIG. 3C is a chart of the Raman spectroscopy spectrum of a graphene before chemical modification.

That is, a chart of the Raman spectroscopy spectrum of a graphene before chemical modification used in Examples to be described later ("xGnP-M5"; manufactured by New Metals and Chemicals Corporation, Ltd.) is shown in FIG. 3C. The value of the ratio (g/d) of the intensity "g" of the peak 501 of the G band of the graphene to the intensity "d" of the peak 502 of the D band thereof is 1.0.

In addition, in a modified graphene obtained through the introduction of a modifying group into the above-mentioned graphene by a method according to one aspect of the present disclosure to be described later, as shown in FIG. 3A, the intensity "g" of the peak 301 of its G band became larger than the intensity "d" of the peak 302 of its D band, and hence the ratio (g/d) became 1.1.

Meanwhile, as described in Japanese Patent No. 5098064, in a modified graphene having introduced thereinto a modifying group by Hummers' method, the intensity "d" of the peak 402 of its D band became stronger than the intensity "g" of the peak 401 of its G band, and hence the ratio (g/d) was 0.7 as shown in FIG. 3B. This is assumed to be because the $sp^2$ structure peculiar to the graphene was broken by the oxidation method as described in the foregoing.

As described above, the modified graphene according to one aspect of the present disclosure is modified without the breakage of a structure inherent in a graphene and the occurrence of a defect in the structure. Accordingly, it can be said that functionality such as satisfactory dispersibility in a dispersion medium is imparted to the graphene without the impairment of characteristics inherent in the graphene.

The ratio (g/d) in the modified graphene according to one aspect of the present disclosure is preferably 1.1 or more.

In the formula (I), the arylene group in the Ar1 is not particularly limited, but examples thereof include the following groups: a phenylene group, a biphenylene group, a triphenylene group, a naphthalene group, and an anthracene group.

In addition, in the formula (I), the linear, branched, or cyclic alkylene group having 1 to 20 carbon atoms in the X1, is not particularly limited, but examples thereof include the following groups: primary to tertiary alkylene groups, such as a methylene group, an ethylene group, a n-propylene group, an iso-propylene group, a n-butylene group, a sec-butylene group, a tert-butylene group, an octylene group, a dodecylene group, a nonadecylene group, a cyclobutylene group, a cyclopentylene group, a cyclohexylene group, a methylcyclohexylene group, a 2-ethylpropylene group, and a 2-ethylhexylene group.

In addition, in the formula (I), the group in the X1, which is obtained by substituting at least one carbon atom in a linear, branched, or cyclic alkylene group having 1 to 20 carbon atoms with at least one structure selected from the group consisting of —O—, —NH—,

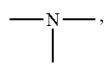

—CO—, —COO—, —CONH—, and an arylene group, is not particularly limited, but examples thereof include the following groups: when one carbon atom forming an ethylene group is substituted with —O—, the group is a methyl ether group; and when one carbon atom forming a propylene group is substituted with —O—, the group is an ethyl ether group.

In the formula (I), the acyl group in the Y1 is not particularly limited, but examples thereof include a formyl group, an acetyl group, a propionyl group, a benzoyl group, and an acrylic group. In addition, in the formula (I), the amide group in the Y1 is not particularly limited, but is a group represented by —CONR'R", and examples thereof include the following groups: a carboxylic acid dialkylamide group in which both of the R' and the R" each represent a methyl group, an ethyl group, a propyl group, a butyl group, or the like; a carboxylic acid monoalkylamide group in which one of the R' and the R" represents a methyl group, an ethyl group, a propyl group, a butyl group, or the like; and an acetamide group in which both of the R' and the R" each represent H.

In addition, in the formula (I), the vinyl group in the Y1 is not particularly limited, but may be, for example, a substituted vinyl group as well as an unsubstituted vinyl group. Examples thereof include a butylene group, a vinyl acetate group, a butyl vinyl ether group, an acrylic group, a methacrylic group, and a styrene group.

In addition, in the formula (I), the carboxylic acid ester group in the Y1 is not particularly limited, but examples thereof include the following groups: a methoxycarbonyl group, an ethoxycarbonyl group, an isopropyloxycarbonyl group, a propoxycarbonyl group, and a cyclohexyloxycarbonyl group.

In addition, in the formula (I), specific examples of the alkylsilyl group having 3 to 6 carbon atoms in the Y1 include a trimethylsilyl group and a triethylsilyl group.

Further, the siloxane group in the Y1 is a group having the following structure.

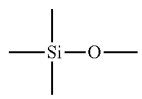

In the formula (I), a substituent on Si of the siloxane group in the Y1 is not particularly limited, but is preferably an alkyl group, a cycloalkyl group, or an aryl group. The contents of the alkyl group and the aryl group are the same as described above. Specific examples of the cycloalkyl group include a cyclopentyl group and a cyclohexyl group. Specific examples of the siloxane group include a trimethylsiloxane group, a triethylsiloxane group, a phenyl-dimethylsiloxane group, and a cyclopentyl-dimethylsiloxane group.

In addition, siloxane groups represented by the formula (II), the formula (III), and the formula (IV) below have large molecular weights, and hence may each be suitably used for the purpose of, for example, preventing the aggregation of the molecules of the graphene or improving compatibility between the graphene and a resin.

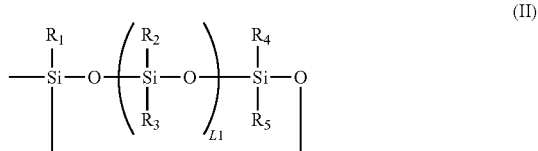

(II)

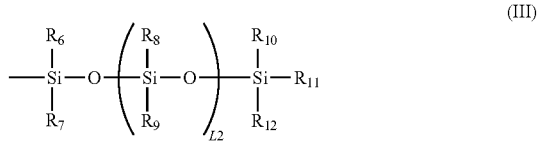

(III)

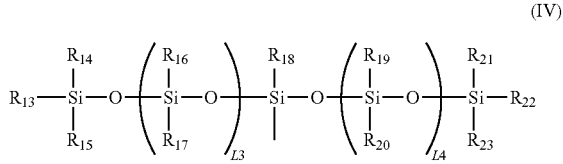

(IV)

In the formulae (II) to (IV), $R_1$ to $R_{23}$ each independently represent an alkyl group, an amino group, a vinyl group, a carboxylic acid ester group, a carboxylic acid group, a hydroxy group, or an aryl group, L1 represents an integer of from 1 to 6, and L2 and (L3+L4) each represent a number of from 0 to 650.

Specific examples of the alkyl group, the vinyl group, the carboxylic acid ester group, and the aryl group are the same as the above-mentioned contents.

The amino group is a group having the following structure, and two substituents on N are each a hydrogen atom or an alkyl group. Specific examples of the alkyl group are the same as the above-mentioned contents.

It is preferred that when the Y1 in the formula (I) represents a group, the number of moles of the group with respect to 1 g of the modified graphene be 0.10 mmol or more and 1.20 mmol or less.

When the number of moles of the group with respect to 1 g of the modified graphene is 0.10 mmol or more, a repulsion (repulsive force) between the molecules of the modified graphene can be secured. As a result, when the modified graphene according to one aspect of the present disclosure is dispersed in a medium or a resin, the formation of a bulk material (aggregate) by a van der Waals force between the molecules of the modified graphene can be suppressed. In addition, when the number of moles of the group is 1.20 mmol or less, a reduction in mutual heat transmission between the molecules of the modified graphene by the covering of the modified graphene with the modifying group can be suppressed. As a result, a reduction in thermal conductivity of a dispersion of the modified graphene according to one aspect of the present disclosure can be suppressed.

Preferred specific examples of the modified graphene according to one aspect of the present disclosure represented by the following formula (I) are represented below. The Gr1 (graphene) in the formula (I) is omitted, and only the structure *Ar1-X1-(Y1)$_{n1}$ is described. The * means a bonding site with a carbon atom forming the Gr1.

Gr1-Ar1-X1-(Y1)$_{n1}$     (I)

(Specific Examples of Modified Graphene)

A1-1 to A1-90 are given below as specific examples of the modified graphene, but the modified graphene is not limited to the following examples.

A1-1
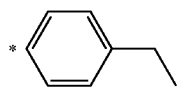

A1-2
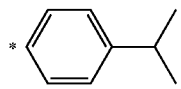

A1-3
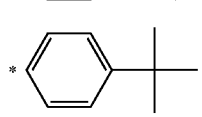

A1-4
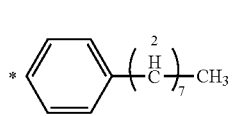

A1-5
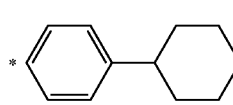

A1-6
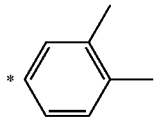

A1-7
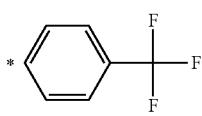

A1-8
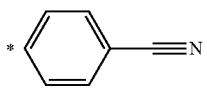

A1-9
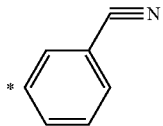

A1-10
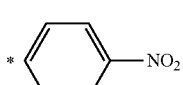

A1-11
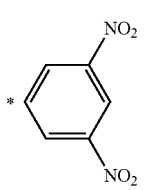

A1-12
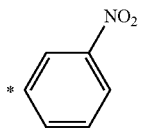

A1-13
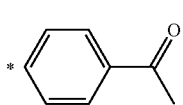

A1-14
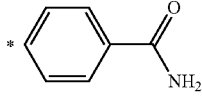

A1-15
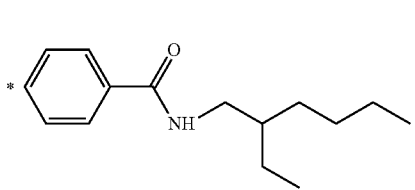

A1-16
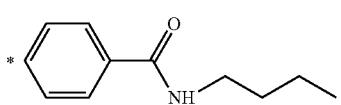

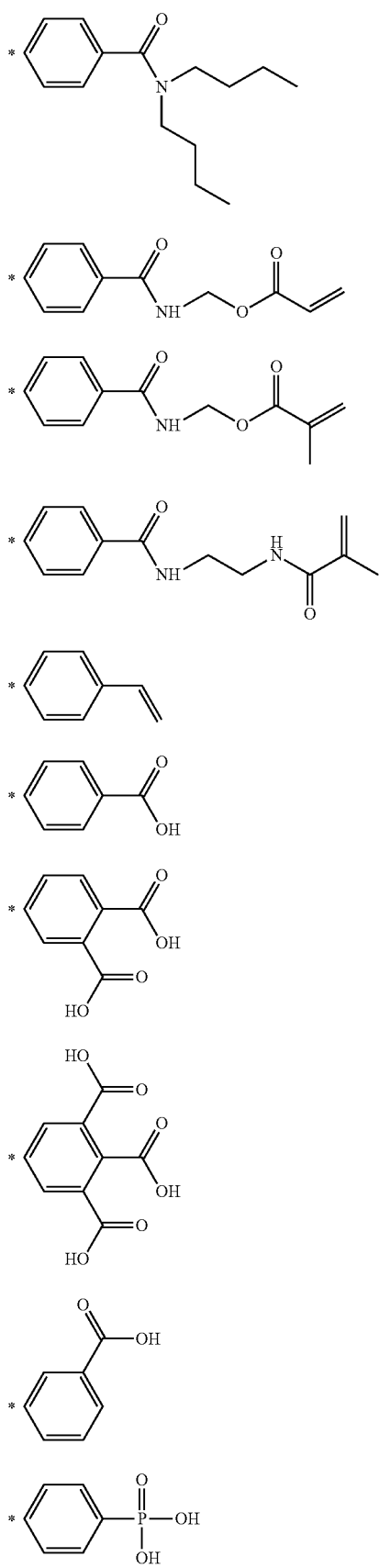
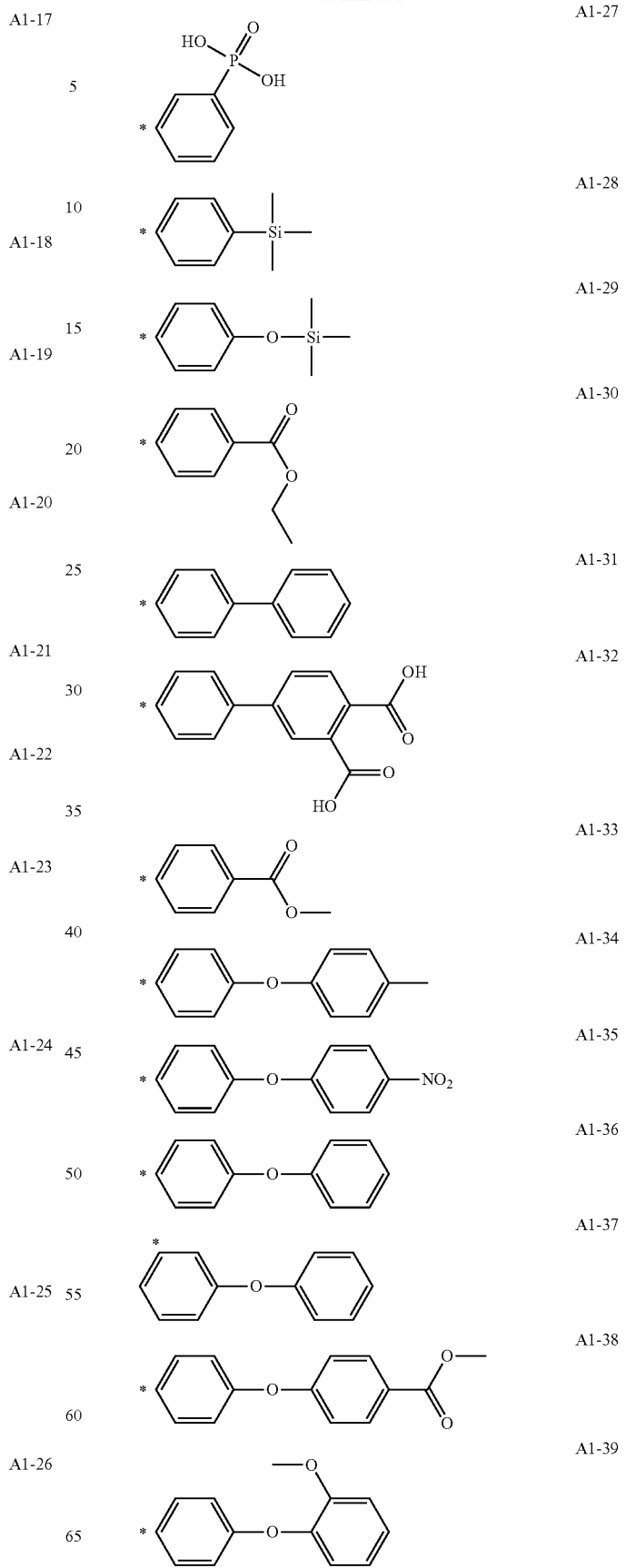

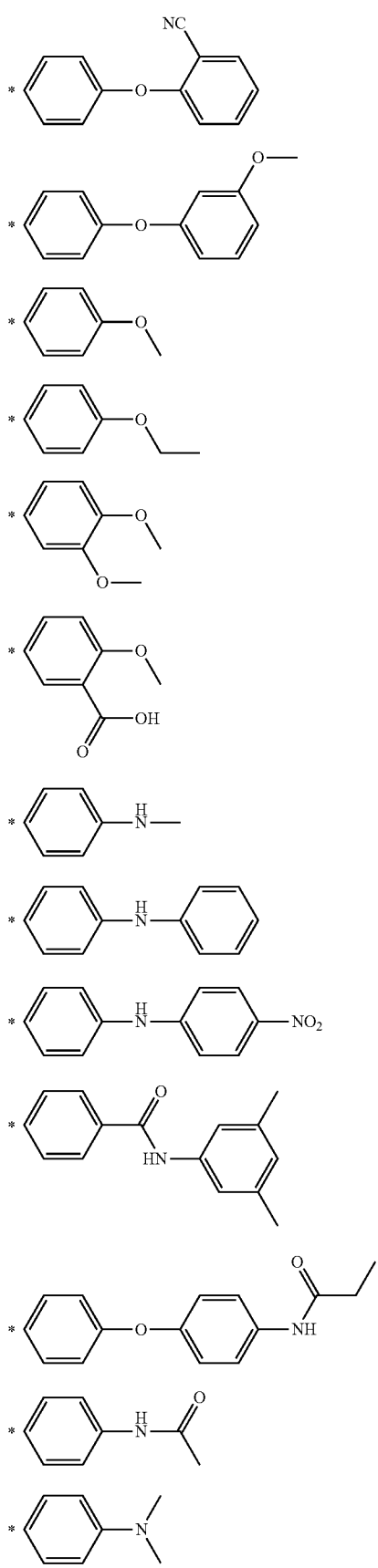
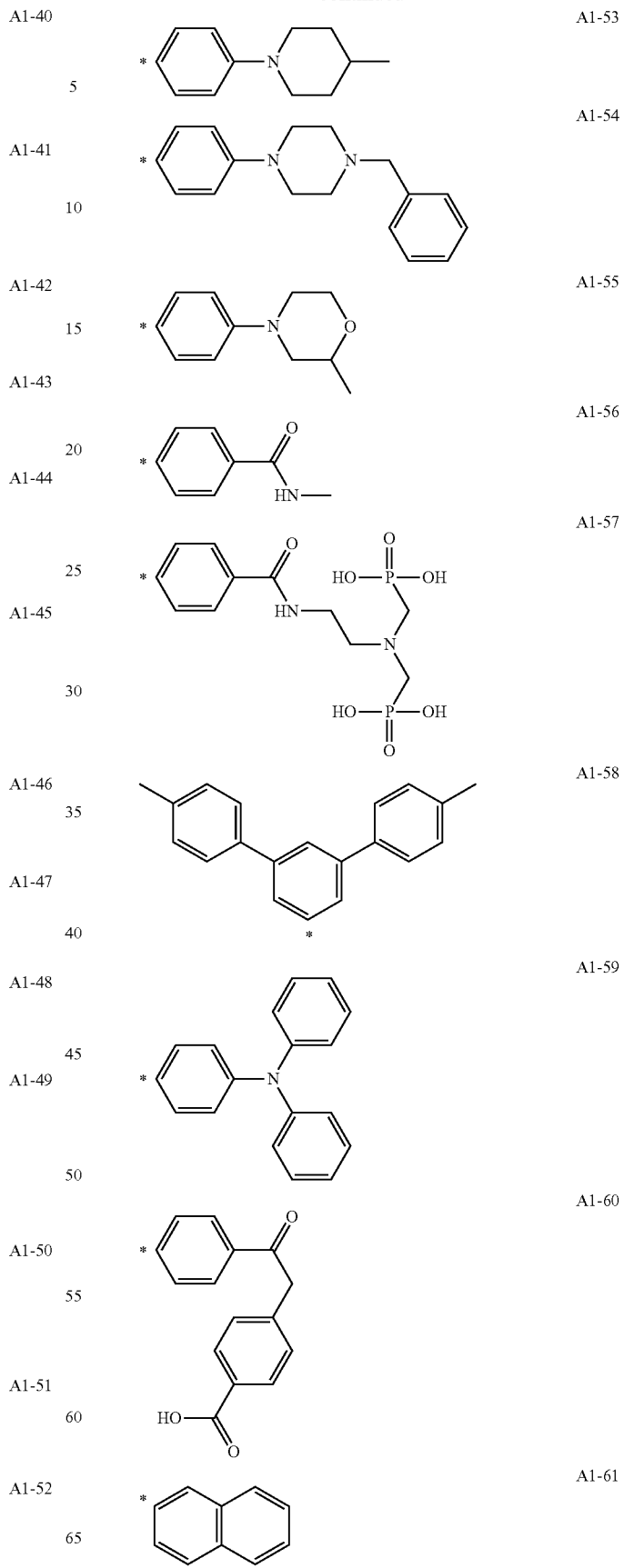

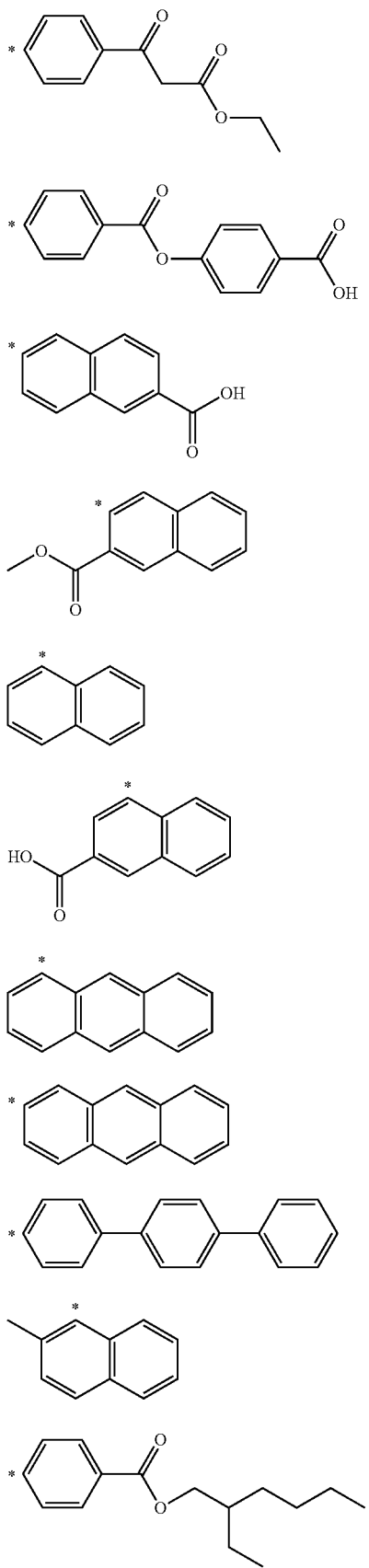
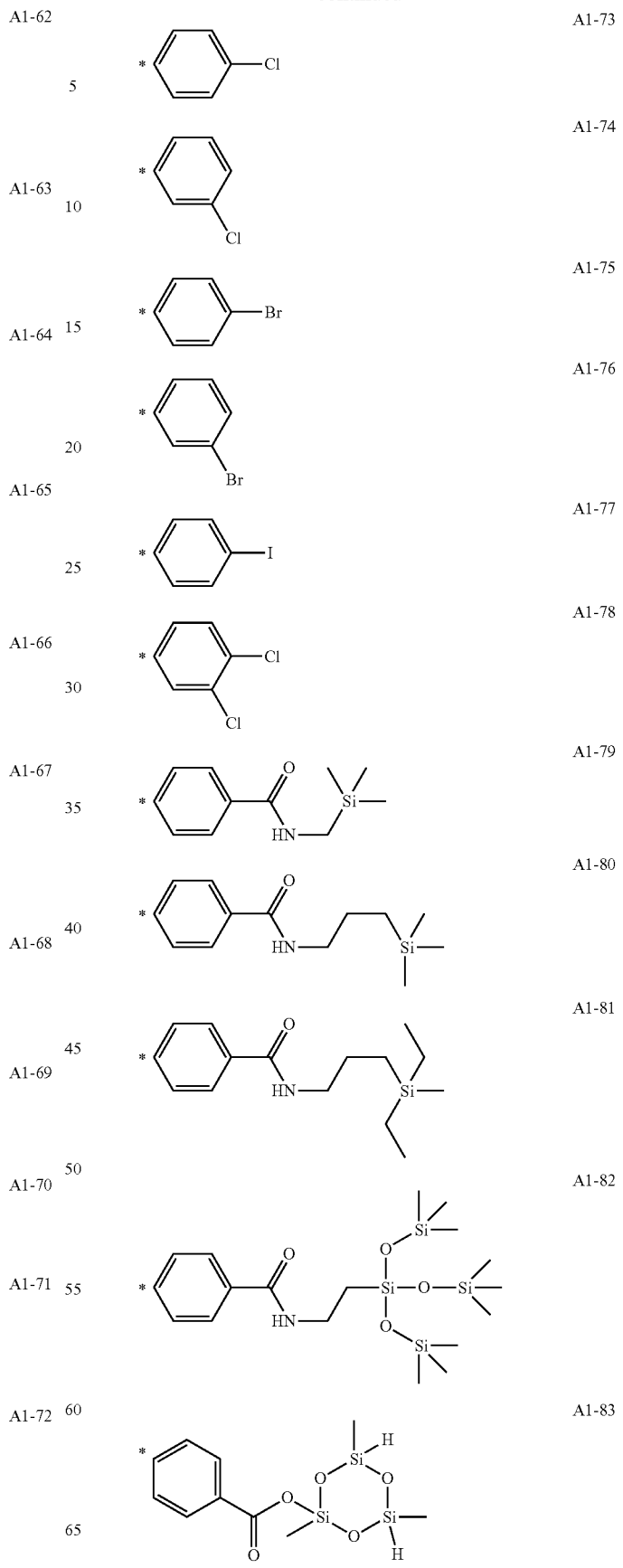

A1-84
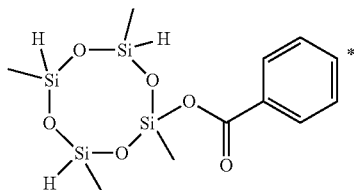

A1-85
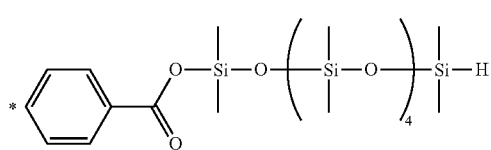

A1-86
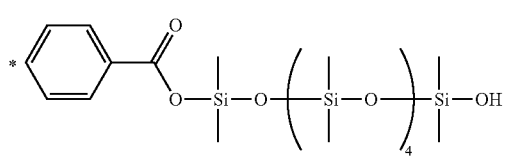

A1-87
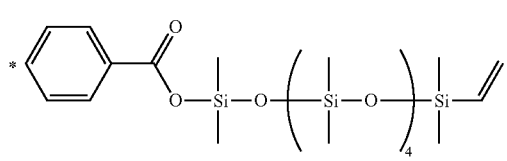

A1-88
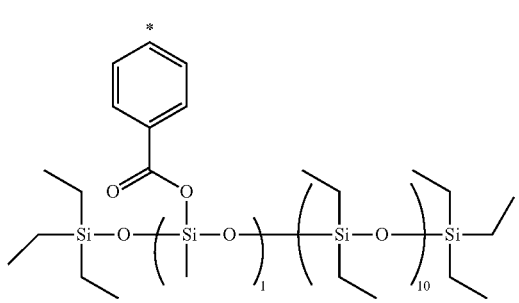

A1-89
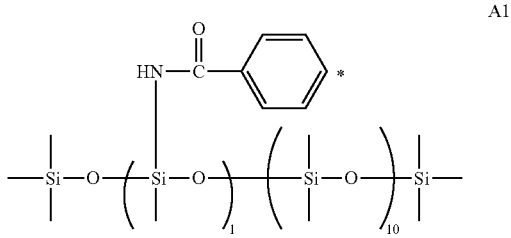

A1-90
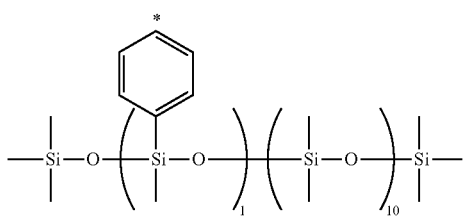

Examples in each of which the Ar1 represents a phenylene group, the X1 represents a single bond, the Y1 represents a carboxylic acid group, and the n1 represents from 1 to 6 correspond to A1-22, A1-23, A1-24 and A1-25.

An example in which the Ar1 represents a phenylene group, the X1 represents a group obtained by substituting at least one carbon atom in a branched alkylene group having 1 to 20 carbon atoms with

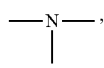

or —CONH—, the Y1 represents a phosphoric acid group, and the n1 represents from 1 to 4 corresponds to A1-57.

Examples in each of which the Ar1 represents a phenylene group, the X1 represents a single bond, the Y1 represents a nitro group, and the n1 represents from 1 to 3 correspond to A1-10, A1-11, and A1-12.

Examples in each of which the Ar1 represents a phenylene group, the X1 represents a group obtained by substituting at least one carbon atom in a branched alkylene group having 1 to 20 carbon atoms with

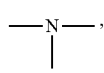

—CO—, or —CONH—, the Y1 represents a hydrogen atom or a vinyl group, and the n1 represents from 1 to 3 correspond to A1-13, A1-14, and A1-15.

The modified graphene including the structure represented by the formula (I) may be synthesized as described below.

<Modified Graphene Production Method (1)>

A method of producing a modified graphene according to a first embodiment of the present disclosure includes a step of bonding a group represented by A1 in the following formula (V) to a carbon atom of a surface of a graphene through a radical addition reaction based on abstraction of a hydrogen atom from a compound represented by the following formula (V) in an aqueous system.

$$HN=N-A1 \quad (V)$$

In the formula (V), A1 represents a group represented by —Ar1-X1-(Y1)$_{n1}$. Ar1 represents an arylene group having 6 to 18 carbon atoms.

X1 represents any one selected from a single bond, a linear, branched, or cyclic alkylene group having 1 to 20 carbon atoms, and a group obtained by substituting at least one carbon atom in a linear, branched or cyclic alkylene group having 1 to 20 carbon atoms with at least one structure selected from the group consisting of —O—, —NH—,

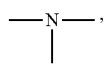

—CO—, —COO—, —CONH—, and an arylene group.

Y1 represents, when the X1 represents a single bond, an atom or a group bonded to at least one carbon atom in the Ar1, or when the X1 does not represent a single bond, an atom or a group bonded to a carbon atom of the X1, and the Y1 represents at least one atom or group selected from the group consisting of a hydrogen atom, a fluorine atom, a chlorine atom, a bromine atom, and an iodine atom, a fluoroalkyl group having 1 to 6 carbon atoms, a cyano group, a nitro group, an acyl group, an amide group, a vinyl group, a carboxylic acid group, a carboxylic acid ester group, and a phosphoric acid group, an alkylsilyl group having 3 to 6 carbon atoms, an alkylsilyl ether group having 3 to 6 carbon atoms, and a siloxane group.

n1 represents an integer of 1 or more, and when the n1 represents 2 or more, the Y1s may represent groups identical to each other or groups different from each other.

The method of producing a modified graphene according to this embodiment may further include a step of producing the compound represented by the formula (V) through abstraction of a hydrogen atom from a compound represented by the following formula (VI).

$$H_2N-NH-A1 \qquad (VI)$$

The compound represented by the formula (V) is sometimes referred to as "treatment agent" for the graphene serving as a raw material.

For example, in the case where a modified graphene represented by the following formula (VIII) is produced, when there is nothing wrong with an increase in number of production steps, a modified graphene represented by the following formula (VII) included in the formula (I) is produced in advance. Then, the modified graphene represented by the following formula (VIII) may be derived from the foregoing modified graphene serving as an intermediate by using a further chemical reaction. In this case, a carboxylic acid group is present in the formula (VI), and hence the modified graphene represented by the following formula (VIII) is easily obtained by utilizing a condensation reaction with an amine compound corresponding to a site to which a substituent is to be further bonded.

$$Gr1\text{-}Ar1\text{-}COOH \qquad (VII)$$

$$Gr1\text{-}Ar1\text{-}CO-NH-CH_2-CH_2-CH_2-CH_3 \qquad (VIII)$$

According to the production method according to this embodiment, the modified graphene can be produced in one pot, without the selection of a reaction apparatus and a liquid medium, and with high reaction efficiency even at normal temperature (25° C.). In particular, the reaction efficiency is high, and hence the usage amount of the treatment agent with respect to the graphene can be reduced. In addition, the high reaction efficiency is synonymous with the suppression of the occurrence of a by-product, and hence the purification of the modified graphene after its production is easy. Further, in the production method according to one aspect of the present disclosure, a stable and safe treatment agent is used, and hence a burden on an environment can be alleviated.

(Graphene)

The graphene serving as a raw material is described. The graphene is a two-dimensional sheet-shaped carbon compound having a structure paved with carbon six-membered rings. In one aspect of the present disclosure, the graphene is not particularly limited as long as the graphene has the structure, and the graphene may be, for example, a single-layer graphene, a multilayer graphene, or graphite.

The single-layer graphene refers to a one atom-thick sheet of $sp^2$-bonded carbon atoms. The multilayer graphene means a laminated sheet of several single-layer graphenes. The graphite means a laminated sheet of more single-layer graphenes than that of the multilayer graphene, or an aggregate of the laminated sheets. In addition, the form of the graphene is not particularly limited, and examples thereof may include a powdery form and a granular form. A commercial product may be used as any such material, or a product produced by a conventionally used method, such as a microwave CVD method or a normal-pressure CVD method, may be used.

As the above mentioned graphene, for example, the following commercially available products can be suitably employed, but the graphene is not limited thereto.

xGnP-C-750 (length in lateral direction: from 1 μm to 2 am, manufactured by XG Sciences, Inc.), xGnP-H-5 (length in lateral direction: 5 am, manufactured by XG Sciences, Inc.), xGnP-M-5 (length in lateral direction: 5 am, manufactured by XG Sciences, Inc.), xGnP-R-10 (length in lateral direction: 10 am, manufactured by XG Sciences, Inc.), iGrafen-α (manufactured by ITEC Co., Ltd.), iGrafen-αS (manufactured by ITEC Co., Ltd.), Gi-PW-F301 (length in lateral direction: 1 am, manufactured by Ishihara Chemical Co., Ltd.), Graphene C (manufactured by KA Graphene), Graphene Powder (manufactured by Graphene Platform Corporation), Graphene Flower GF4 (length in lateral direction: 10 jam, manufactured by Incubation Alliance Inc.), Graphene Flower GF7 (length in lateral direction: from 1 jam to 3 jam, manufactured by Incubation Alliance Inc.), Expanded Graphite EXP-50S (manufactured by Fujikokuen Kogyo Co., Ltd.), Expanded Graphite EXP-50SL (manufactured by Fujikokuen Kogyo Co., Ltd.), Expanded Graphite EC1 (manufactured by Ito Graphite Co., Ltd.), 0 Spherical Graphite SG-BH (manufactured by Ito Graphite Co., Ltd.), Spherical Graphite SG-BH8 (manufactured by Ito Graphite Co., Ltd.), Spherical Graphite CGB20 (particle diameter: 20 μm, manufactured by Nippon Graphite Industries, Co., Ltd.), Spherical Graphite CGC20 (particle diameter: 20 μm, manufactured by Nippon Graphite Industries, Co., Ltd.), and Graphene CVD Mono-layer Sheet (manufactured by New Metals and Chemicals Corporation, Ltd.).

(Treatment Agent)

Commercial reagents may be used as the compounds represented by the formula (V) and the formula (VI). In addition, when the compounds are not commercially available as reagents, synthesized compounds may be used.

Methods for the synthesis are not particularly limited, but are described below by taking an example. A synthesis method represented in the following formula 2 is a method involving obtaining a hydrazine compound from an amine compound. The method is specifically described by taking a case in which 4-hydrazinobenzoic acid is synthesized from 4-aminobenzoic acid as an example. Hydroxylamine-o-sulfonic acid is used as a nitrogen source at the time of the addition of nitrogen to the amine compound. When the amine compound and hydroxylamine-o-sulfonic acid are caused to react with each other under an alkaline condition, the hydrazine compound is produced. When the hydrazine compound is precipitated as a salt (e.g., a hydrochloride) thereof by adding an acid, the hydrazine compound may be efficiently fractionated through filtration or the like.

Synthesis method formula 2

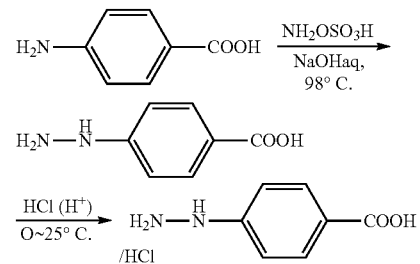

In addition, in, for example, the Journal of the American Chemical Society, 76, 1283-1285 (1954), there is a description of a method involving obtaining 2-hydrazino-1-propanol from 2-amino-1-propanol through the use of hydroxylamine-o-sulfonic acid.

(Oxidant)

In the production method according to this embodiment, the production of the modified graphene is preferably performed in the presence of an oxidant. The term "oxidant" means a "compound that can abstract a hydrogen atom or an electron from a compound of interest, and that has an oxidation potential of +0.00 V or more." The oxidant may be used for improving a reaction rate, but the reaction to be utilized in the production method according to this embodiment proceeds without the use of any oxidant.

In general, when an oxidant is caused to act on a graphene, carbon atoms on the surfaces of the particles of the graphene are oxidized to provide carboxylic acid groups. Meanwhile, in the production method according to one aspect of the present disclosure, the production of the compound represented by the formula (V) from the compound represented by the formula (VI) is accelerated by the action of the oxidant, and hence an oxidative radical addition reaction that proceeds following the production preferentially proceeds.

Therefore, the oxidant does not directly act on the surface of the graphene. This is because energy needed for abstracting a hydrogen atom from each of the compounds represented by the formulae (V) and (VI) is smaller than energy (bond energy between carbon and oxygen) needed for oxidizing a carbon atom on the surface of the graphene to derive a carbonyl species (C=O). That is, when the compounds represented by the formulae (V) and (VI) are present, the oxidant is selectively consumed in the abstraction of a hydrogen atom.

Examples of the oxidant that may be used in the production method according to this embodiment may include a halogen, an oxoacid compound, a metal oxide, a metal halide compound, a metal porphyrin compound, a hexacyano metal acid compound, a metal nitrate, hydrogen peroxide, and nitric acid.

Examples of the halogen include chlorine, bromine, and iodine.

Examples of the oxoacid compound may include chromic acid, molybdic acid, permanganic acid, vanadic acid, bismuthic acid, a hypohalous acid, a halous acid, a halogen acid, and a perhalic acid. Each of those oxoacid compounds may form a salt, but is required to include a metal. As a cation with which each of the oxoacid compounds forms a salt, there may be given, for example, an alkali metal ion and an ammonium ion. The salt may be present in an aqueous liquid in the form of being dissociated into ions, but for convenience, is represented as "salt". Specific examples of the oxoacid compound may include the following compounds: chromic acid salts, such as potassium chromate, potassium dichromate, bis(tetrabutylammonium) dichromate, pyridinium dichromate, pyridinium chlorochromate, and pyridinium fluorochromate; permanganic acid salts, such as potassium permanganate, sodium permanganate, ammonium permanganate, silver permanganate, zinc permanganate, and magnesium permanganate; vanadic acid salts, such as ammonium vanadate, potassium vanadate, and sodium vanadate; bismuthic acid salts, such as sodium bismuthate and potassium bismuthate; and hypochlorous acid, chlorous acid, perchloric acid, hypobromous acid, bromous acid, bromic acid, perbromic acid, hypoiodous acid, iodous acid, iodic acid, periodic acid, hypofluorous acid, and salts thereof.

Examples of the metal oxide may include manganese oxide, lead oxide, copper oxide, silver oxide, and osmium oxide. Examples of the metal halide compound may include zinc chloride, aluminum chloride, silver chloride, chromium chloride, zirconium chloride, tin chloride, cerium chloride, iron chloride, barium chloride, magnesium chloride, and manganese chloride.

The metal porphyrin compound may be, for example, a porphyrin compound that has a central metal and may be substituted. Specific examples thereof may include a tetrabenzoporphyrin compound, a tetraazaporphyrin compound, a phthalocyanine compound, and a naphthalocyanine compound. The central metal only needs to be such a metal that the oxidation potential of the metal porphyrin compound becomes +0.00 V or more. Examples of the central metal may include Fe, Co, Ni, Cu, Zn, Mg, Pt, Mn, Ru, Cr, and Pd. In addition, a ligand may be present on the metal, and a known ligand only needs to be used as the ligand.

Examples of the hexacyano metal acid compound may include hexacyanoferrate salts and hydrates thereof. Specific examples thereof may include potassium hexacyanoferrate, sodium hexacyanoferrate, ammonium hexacyanoferrate, copper hexacyanoferrate, double hexacyanoferrates (e.g., lithium potassium hexacyanoferrate), and hydrates thereof.

Examples of the metal nitrate may include potassium nitrate, sodium nitrate, silver nitrate, and copper nitrate.

In addition to the above-mentioned oxidants, for example, an organic peroxide, a hypervalent iodine compound, or an N-oxide compound may be used as long as any such compound corresponds to the definition of the "oxidant" described in the foregoing.

As the oxidation potential of the oxidant becomes larger, a hydrogen atom is more easily abstracted from the treatment agent. The oxidation potential of the oxidant that may be used in this embodiment is +0.00 V or more; an oxidant having an oxidation potential of +0.50 V or more and +1.70 V or less is more preferred because the efficiency of a reaction between the graphene and the treatment agent can be improved. Examples of the oxidant having an oxidation potential in the range may include iron chloride (neutral to alkaline; +0.77 V), sodium periodate (acidic; +1.20 V), manganese oxide (neutral to alkaline; +1.28 V), and potassium permanganate (acidic; +1.51 V).

The reason why the oxidation potential was involved in the reaction was assumed to be as described below.

Energy needed for abstracting a hydrogen atom from a hydrazine compound to turn the compound into a diazene compound was calculated with general-purpose quantum chemical calculation software ("Gaussian 03 Revision E. 01 [structure optimization approach; B3LYP/6-31G*]"; manufactured by Gaussian, Inc.). As a result, it was revealed that energy needed for abstracting two hydrogen atoms therefrom was +1.00 V, and energy needed for abstracting one hydrogen atom therefrom was +0.50 V. Because of such reason, when an oxidant having an oxidation potential of +0.50 V or more is used, a hydrogen atom can be more efficiently abstracted from the hydrazine compound, and hence the reaction efficiency can be improved.

Meanwhile, in the case where an oxidant having an oxidation potential of more than +1.70 V is used, the reaction proceeds, but the hydrogen atom-abstracting action, that is, oxidizing action of the oxidant becomes larger, and hence the hydrazine compound is abruptly radicalized. In this case, a large excess amount of a radical is present in the reaction system, and hence the deactivation reaction of the radical (e.g., a homocoupling reaction between adjacent radical molecules) occurs. Accordingly, the reaction between the graphene and the treatment agent may be inhibited to make it difficult to obtain an improving effect on the reaction efficiency exhibited by the use of the oxidant. Because of such reason, the oxidation potential of the oxidant is preferably +1.70 V or less. In particular, the oxidation potential of the oxidant is more preferably +1.00 V or more and +1.60 V or less.

An oxidant having a catalytic action is also preferably used. Of the oxidants listed above, for example, a metal halide compound, a metal porphyrin compound, or a hexacyano metal acid compound of at least one kind of metal selected from the group consisting of Fe, Co, Ni, Cu, Mg, Mn, Cr, and Mo has a catalytic action. The oxidant having a catalytic action is used in the abstraction of a hydrogen atom to become a reduced species, and is then subjected to the action of oxygen in the reaction system to return to an oxidized species. Accordingly, the oxidant can be used as an oxidant again. Therefore, the use of the oxidant having a catalytic action can reduce the usage amount of the oxidant. The oxidant having a catalytic action has a metal whose valence easily changes (metal element that can adopt two or more oxidation states).

Specific examples of the change in valence of the metal include: Fe (II, III); Co (II, III); Ni (II, III); Cu (0, I, II); Mg (0, II); Mn (II, IV, VII); Cr (II, III); and Mo (IV, V). The mechanism via which the catalytic action of the oxidant occurs is described by way of a specific example. In the case of, for example, an oxidant having trivalent Fe (Fe(III)), $Fe^{3+}$ (Fe(III)) that is an oxidized species is used in the abstraction of a hydrogen atom from the hydrazine compound to produce $Fe^{2+}$ (Fe(II)) that is a reduced species. After that, the reduced species is subjected to the action of oxygen in the reaction system to return to $Fe^{3+}$ (Fe(III)) that is an oxidized species. Accordingly, the oxidant can be used as an oxidant again.

In the production method according to this embodiment, an inert gas, such as nitrogen or argon, may be utilized because even when the oxidant is used, its function is not impaired. This is because the oxidative radical addition reaction is performed not by oxygen exchange but by the abstraction of a hydrogen atom. Examples of a method of introducing the inert gas into the reaction system include: a method involving flowing the gas from a bomb into the system through a tube; and a method involving flowing the gas collected in a balloon or the like into the system through a needle tip.

(Reaction Mechanisms)

Reaction mechanisms in obtaining the modified graphene according to this embodiment are described below. As illustrated in FIG. 1, the reaction according to this embodiment can be assumed to proceed via an oxidative radical addition reaction. The reaction mechanisms illustrated in FIG. 1 are an example when the compound represented by the formula (VI) is used.

First, a hydrogen atom of a hydrazine compound represented by (1) in FIG. 1 is abstracted by the action of an oxidant ($Fe^{3+}$). Thus, the compound is radically oxidized to produce a diazene compound (2). A hydrogen atom is abstracted from the compound by a further oxidizing action. Thus, a diazene radical (3) is produced. The diazene radical instantly causes nitrogen desorption to produce a radical species (4). Then, the radical addition of the radical species (4) to a double bond on the surface of a graphene particle occurs to provide a target modified graphene (6) via a radical intermediate (5).

When an oxidant whose valence easily changes, such as potassium hexacyanoferrate(III), is used in the production method according to this embodiment, an addition reaction different from that described above may occur in parallel therewith. That is, simultaneously with the production of the radical intermediate (5) by the radical addition of the radical species (4) to the double bond on the surface of the graphene particle, a radical is scavenged by an oxygen molecule to produce a radical intermediate (7). In this case, the intermediate is reduced by the action of the reduced species ($Fe^{2+}$) of the oxidant, and then a modified graphene (9) having bonded thereto a hydroxy group is obtained via an oxygen radical intermediate (8).

In contrast, when an oxidant such as hypochlorous acid is used, the amount of the modified graphene (9) to be produced is substantially zero.

In the above-mentioned respective reaction mechanisms, the diazene compound and the hydrazine compound do not abruptly decompose, and the radical species is slowly produced. Accordingly, the radical addition reaction to the surface of the graphene particle efficiently proceeds. Therefore, according to the production method according to this embodiment, even when the usage amount of the treatment agent with respect to the graphene is smaller than that in a related-art production method, a modified graphene having introduced thereinto a large amount of the substituent, that is, the A1 can be obtained.

In a technology disclosed in Japanese Patent No. 3980637, a graphene is modified by using a diazonium salt as a treatment agent. However, the diazonium salt is liable to decompose under the influence of an alkali or a temperature of more than normal temperature (25° C.). When the diazonium salt decomposes in a reaction system, various decomposed products are produced. Accordingly, a reaction between any one of the decomposed products and a liquid medium or oxygen, a reaction between the decomposed products, and a side reaction except the foregoing are liable to occur. Therefore, when an attempt is made to obtain a modified graphene having introduced thereinto a large amount of the substituent through the use of the diazonium salt, the diazonium salt needs to be used in a large amount with respect to the graphene. However, when the usage amount of the diazonium salt is increased, an encounter with the following problem occurs: many bubbles of a nitrogen gas are produced in the graphene, and hence it becomes difficult to improve the efficiency of a reaction between the graphene and the salt.

In the production method according to this embodiment, in order to control the reaction rate of the radical addition reaction, the temperature at which the reaction is performed may be set to a value except normal temperature (25° C.). When the reaction rate is to be increased, the temperature only needs to be increased, and the liquid medium only needs to be heated at a temperature in a range equal to or less than the reflux temperature of the liquid medium. For example, when the liquid medium is water, the temperature only needs to be set to 100° C. or less. In addition, when the liquid medium is tetrahydrofuran, the temperature only needs to be set to 80° C. or less. Further, when the liquid medium is N,N-dimethylformamide, the temperature only needs to be set to 160° C. or less. However, the efficiency of the reaction to be utilized in the production method according to this embodiment is high even around normal temperature (25° C.), and hence there is no need to increase the temperature to a very high value. Further, no matter how chemically stable the graphene may be, the reaction is preferably performed at 80° C. or less in consideration of its thermal decomposition. Meanwhile, when the reaction rate is to be reduced, the liquid medium only needs to be cooled so that its temperature may be normal temperature (25° C.) or less. However, a long reaction time may be required, and hence the temperature is preferably set to −5° C. or more.

The production method according to this embodiment is typically performed in the liquid medium. The content (mass %) of the graphene in the liquid medium is preferably 1.0 mass % or more and 50.0 mass % or less, more preferably 5.0 mass % or more and 40.0 mass % or less with respect to the total mass of the liquid medium. When the content is excessively high, the viscosity of the reaction system may increase to make it difficult to stir the system, thereby reducing the reaction efficiency to some extent. Meanwhile, when the content is excessively low, the frequency at which the treatment agent and the graphene are brought into contact with each other in the reaction system may reduce to reduce the reaction efficiency to some extent.

(Posttreatment)

The modified graphene thus produced may be suitably used in various applications after having been subjected to a general posttreatment method, such as purification. Specifically, the modified graphene may be brought into a normal state, such as a powdery state or pellet state in which the liquid medium is absent. In this case, the liquid medium may be removed through a pressure reduction or heating by utilizing an evaporator or the like. Alternatively, the liquid medium may be removed through drying by utilizing a freeze-drying method, an oven, or the like.

<Modified Graphene Production Method (2)>

A method of producing a modified graphene according to a second embodiment of the present disclosure includes a step of causing at least one kind of treatment agent selected from a compound represented by the following formula (IX) and a compound represented by the following formula (X) to react with a graphene to chemically bond a group represented as A1 in the compound represented by the formula (IX) or the formula (X) to a carbon atom of a surface of the graphene.

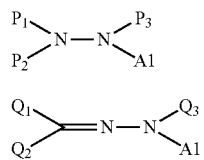

(IX)

(X)

In the formula (IX), $P_1$, $P_2$, and $P_3$ each independently represent a hydrogen atom, an alkyl group, an aryl group, a carboxylic acid ester group, or —S(=O)$_2$—R', and not all of the $P_1$, the $P_2$, and the $P_3$ simultaneously represent hydrogen atoms, and R' represents a hydroxy group, an alkyl group, or an aryl group.

In the formula (X), $Q_1$ and $Q_2$ each independently represent a hydrogen atom, an alkyl group, an aryl group, a halogen atom, a cyano group, a nitro group, an amino group, an alkoxy group, a thioalkoxy group, an acyl group, a carboxylic acid ester group, an aryloxy group, a carboxylic acid group, a sulfonic acid group, a phosphoric acid group, or a phosphonic acid group, and the $Q_1$ and the $Q_2$ do not simultaneously represent hydrogen atoms, and $Q_3$ represents a hydrogen atom, an alkyl group, an aryl group, or a carboxylic acid ester group.

In addition, in each of the formulae (IX) and (X), A1 represents a group represented by —Ar1-X1-(Y1)$_{n1}$ in the formula (I). Accordingly, Ar1, X1, Y1, and n1 are identical in meaning to those in the formula (I).

For example, in the case where a modified graphene represented by the following formula (XIII) is produced, the following procedure may be adopted: a modified graphene represented by the following formula (XII) included in the formula (I) is produced in advance; and the modified graphene represented by the formula (XIII) is derived from the foregoing modified graphene serving as an intermediate by using a further chemical reaction. In this case, a condensation reaction with an amine compound corresponding to a carboxylic acid group in the formula (XII) only needs to be utilized.

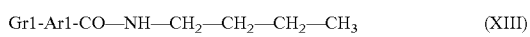

<Reaction Mechanisms>

Figure 2:
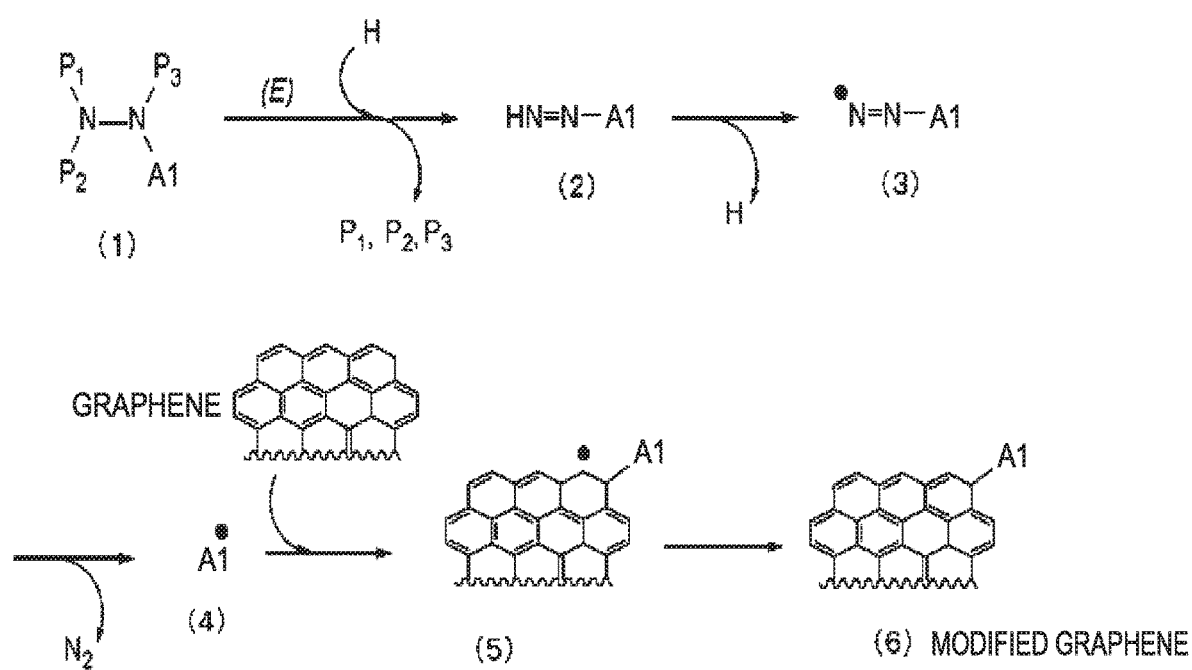
FIG. 2 is a view for illustrating assumed reaction mechanisms in obtaining a modified graphene in the case of using a compound represented by the formula (IX) according to one aspect of the present disclosure.

Reaction mechanisms in obtaining the modified graphene according to this embodiment are described below. As illustrated in FIG. 2, the reaction according to this embodiment can also be assumed to proceed via an oxidative radical addition reaction. The reaction mechanisms illustrated in FIG. 2 are an example when the compound represented by the formula (IX) is used as a treatment agent.

First, when external energy, such as heat or light, is applied from the outside to a treatment agent (1) that is stable at room temperature, the $P_1$, the $P_2$, and the $P_3$ that are substituents on N atoms may desorb to produce a diazene compound (2). Further, the diazene compound (2) undergoes oxidation (hydrogen desorption) to provide a radical intermediate (3), followed by the nitrogen desorption of the radical intermediate (3) to generate a corresponding radical species (4). Then, the addition reaction of the radical species (4) to a double bond of a graphene occurs to provide a modified graphene (6) according to one aspect of the present disclosure via an intermediate (5).

<Reaction and Purification>

The treatment agent to be used in the production method according to this embodiment is stable at room temperature, and hence the reaction is easily controlled by the external energy. In addition, in the production method according to this embodiment, the reaction between the graphene and the treatment agent can be performed in one pot and without the selection of a reaction apparatus and a liquid medium, and hence the modified graphene can be produced with high reaction efficiency. Higher reaction efficiency means that the surface modification of the graphene can be achieved by using a smaller amount of the treatment agent. Accordingly, as the reaction efficiency becomes higher, a merit in terms of cost is obtained, and moreover, the production of impurities by the reaction can be reduced. As the amount of the impurities becomes smaller, the efficiency with which the modified graphene is purified can be improved, and a time for the purification can be shortened.

In the technology disclosed in Japanese Patent No. 3980637, the surface modification of the graphene is performed by using the diazonium salt as a treatment agent. The diazonium salt to be used as a treatment agent undergoes a decomposition accompanied by various side reactions at room temperature. The reactions are difficult to control, and hence when an attempt is made to increase the amount of a substituent to be introduced through the use of the diazonium salt, the diazonium salt needs to be used in an excess amount with respect to the graphene. However, when the usage amount of the diazonium salt is increased in one stroke, the following adverse effect occurs: many bubbles of a nitrogen gas are produced in the graphene, and hence it becomes difficult to improve the efficiency of the reaction between the graphene and the salt.

The treatment agent to be used in the production method according to this embodiment is a compound that has two nitrogen atoms (N—N) in its molecular structure, and that has a structure in which the A1 serving as a functional group to be bonded to the graphene is bonded to a nitrogen atom (N). The treatment agent may have a function of bonding a substituent including a hydrophilic group or a hydrophobic group to the graphene through an oxidative radical addition reaction.

As described above, the treatment agent is chemically stable, and is hence hardly affected by a pH and a temperature. Accordingly, the pH and temperature of the reaction system may be arbitrarily set. Specifically, the pH of the reaction system is preferably from 1 to 13, more preferably from 1 to 10, particularly preferably from 1.5 to 7. To improve the reaction efficiency, the pH of the reaction system is preferably set within an acidic to neutral region. In a high-pH region, such as an alkaline region, the treatment agent may decompose. Meanwhile, when the pH of the reaction system is set to less than 1.5, the solubility of the treatment agent is remarkably poor, and hence a time for the reaction may lengthen. In addition, a large amount of an acidic compound needs to be used, and hence a treatment for the modified graphene, such as purification, may be difficult.

In addition, to control the reaction rate of the radical addition reaction, the temperature of the reaction system may be set to a value except normal temperature (25° C.). The temperature only needs to be appropriately set in accordance with the kind of the treatment agent. Specifically, the temperature is preferably from 5° C. to 80° C., more preferably from 10° C. to 70° C. When the temperature is increased, the reaction rate increases, but a side reaction tends to be liable to occur to reduce the reaction efficiency. Meanwhile, when the temperature is reduced, a side reaction hardly occurs, but the reaction rate tends to reduce to lengthen the reaction time.

The production method according to this embodiment is typically performed in the liquid medium. The content (mass %) of the graphene in the liquid medium is preferably 1.0 mass % or more and 50.0 mass % or less, more preferably 5.0 mass % or more and 40.0 mass % or less with respect to the total mass of the liquid medium. When the content of the graphene is excessively high, the viscosity of the reaction system may increase to make it difficult to stir the system, thereby reducing the reaction efficiency to some extent. Meanwhile, when the content of the graphene is excessively low, the frequency at which the treatment agent and the graphene are brought into contact with each other in the reaction system may reduce to reduce the reaction efficiency to some extent.

<Treatment Agent>

For example, at least one kind selected from the compound represented by the formula (IX) and the compound represented by the formula (X) is used as the treatment agent to be used in the production method according to this embodiment.

Specific structures of the treatment agent represented by the formula (IX) are represented in S1-1 to S1-93. The A1 is in conformity with the specific examples of the formula (I).

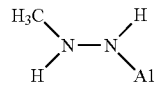
S1-1

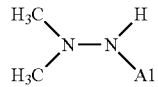
S1-2

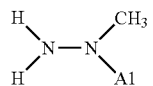
S1-3

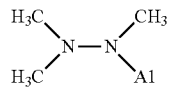
S1-4

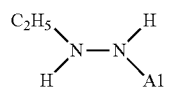
S1-5

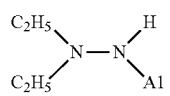
S1-6

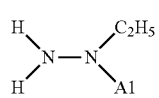
S1-7

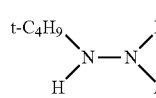
S1-8

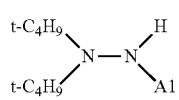
S1-9

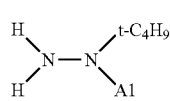
S1-10

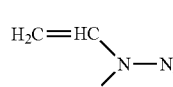
S1-11

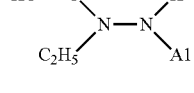
S1-12

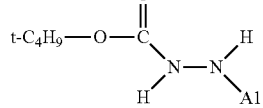
S1-13

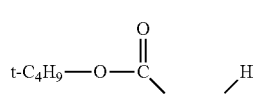
S1-14

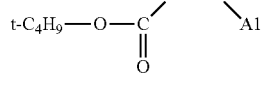
S1-15

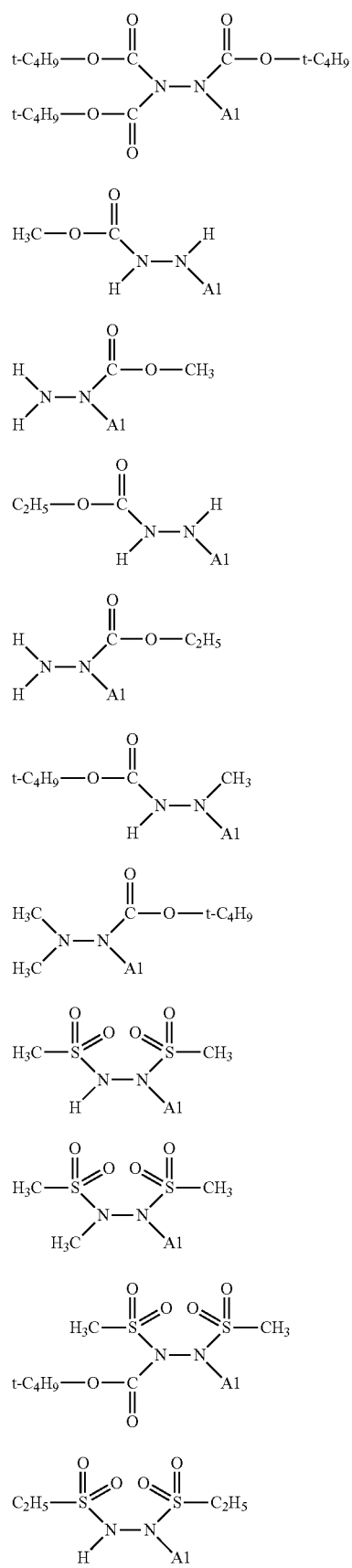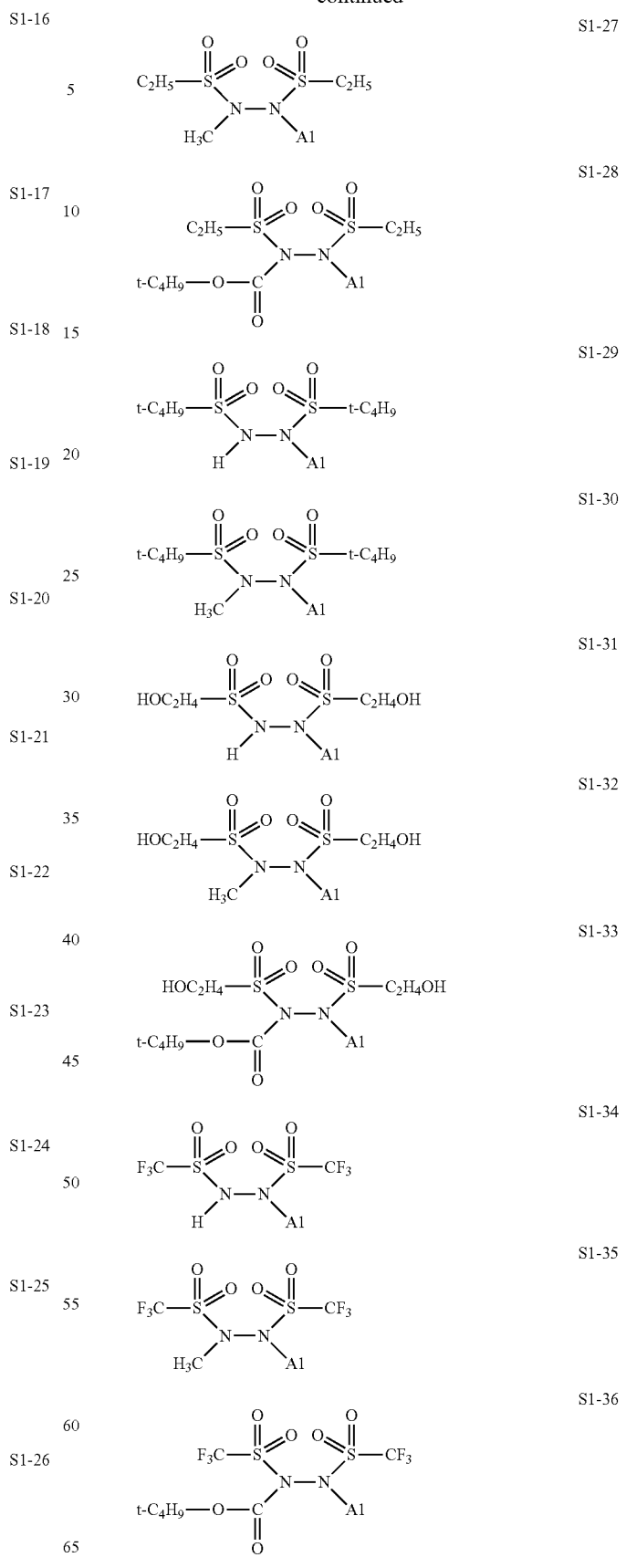

S1-37
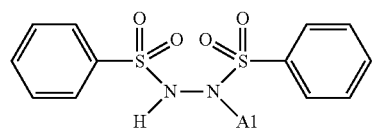
S1-38
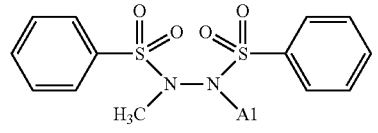
S1-39
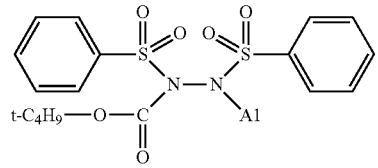
S1-40
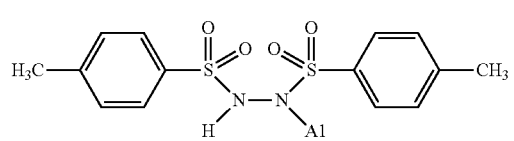
S1-41
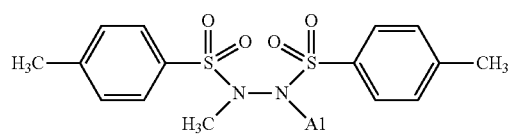
S1-42
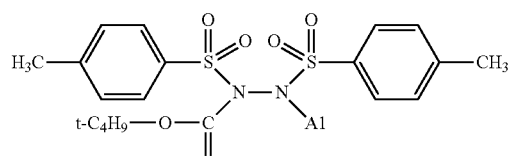
S1-43
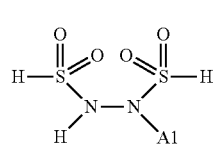
S1-44
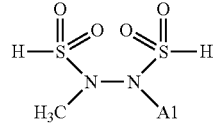
S1-45
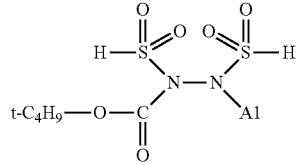
S1-46
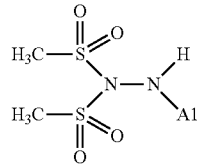
S1-47
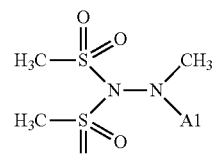
S1-48
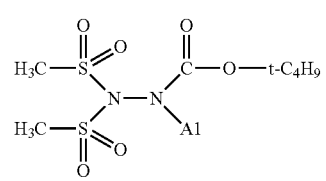
S1-49
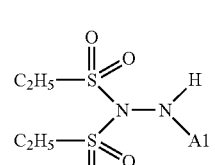
S1-50
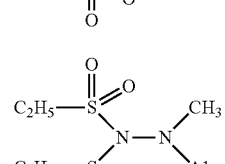
S1-51
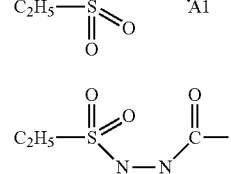
S1-52
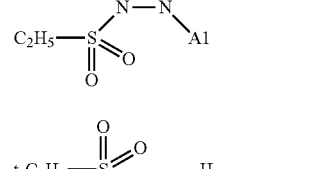
S1-53
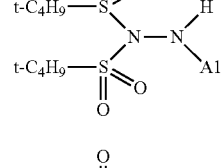
S1-54
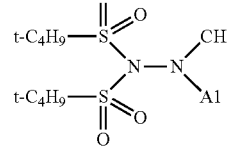
S1-55
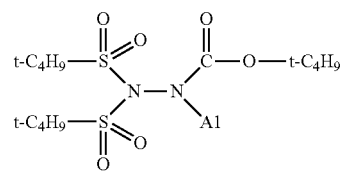

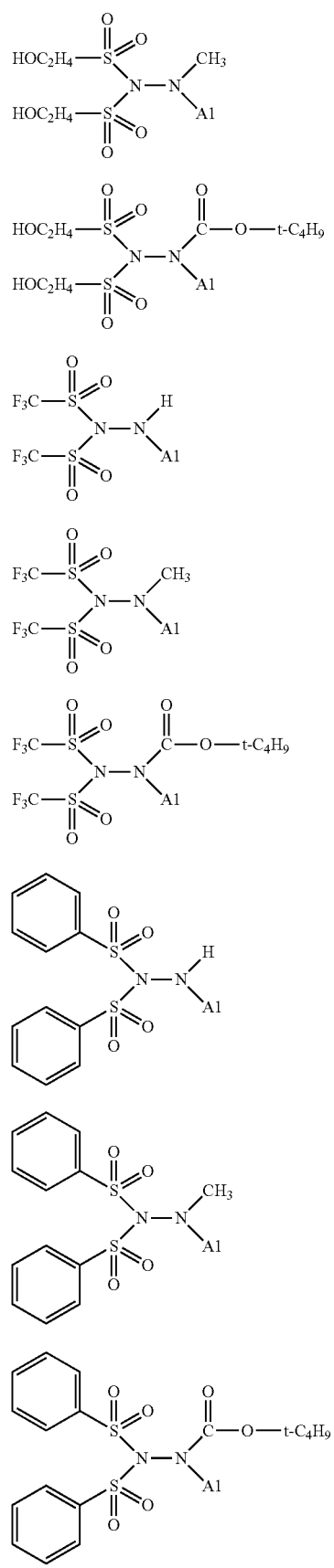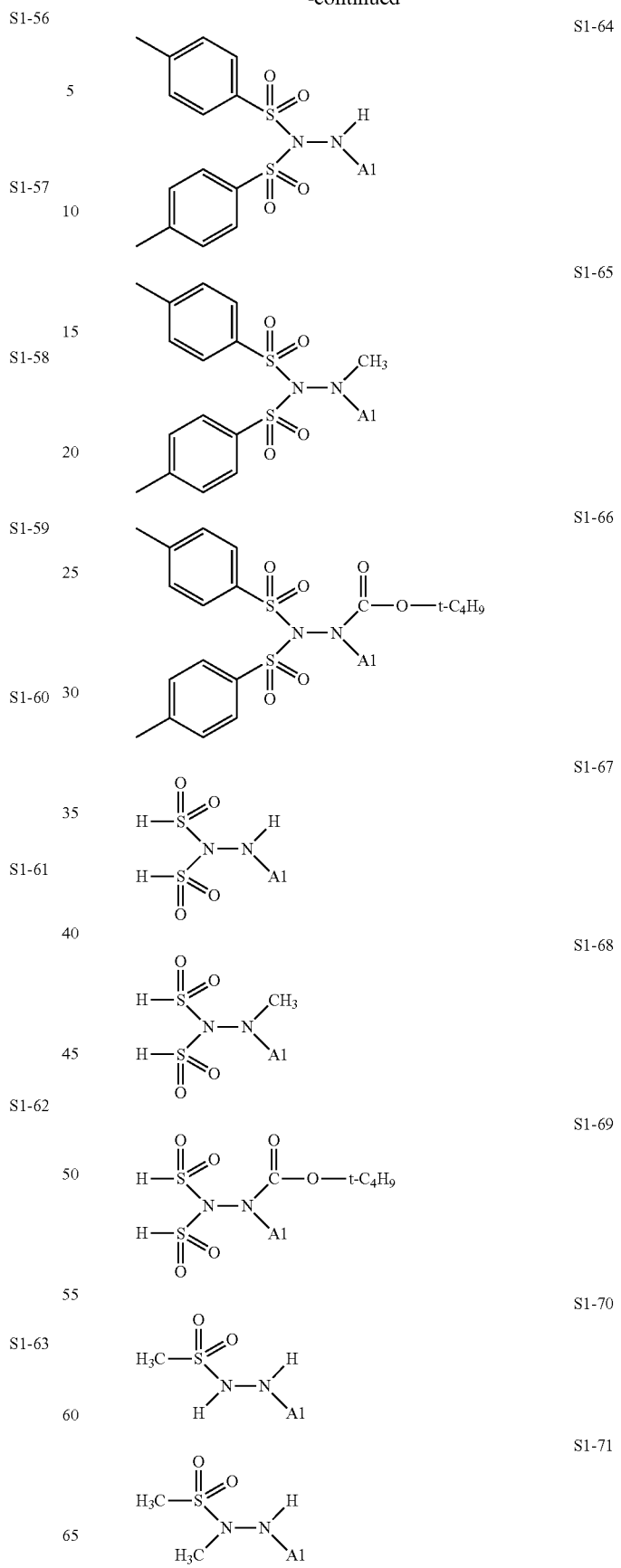

-continued
S1-72 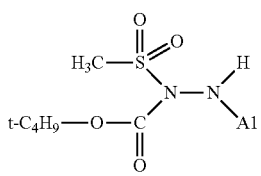
S1-73 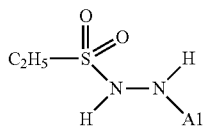
S1-74 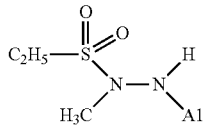
S1-75 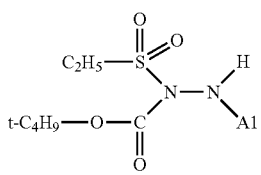
S1-76 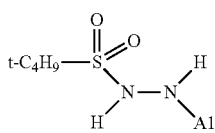
S1-77 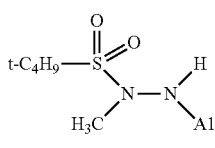
S1-78 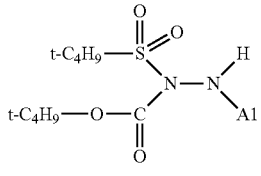
S1-79 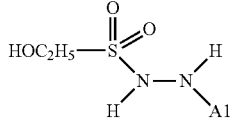
S1-80 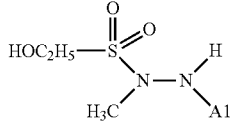
S1-81 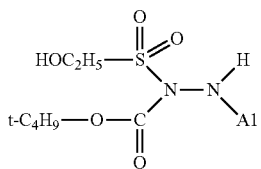
-continued
S1-82 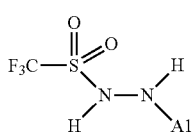
S1-83 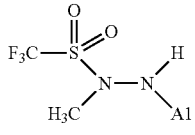
S1-84 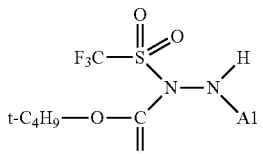
S1-85 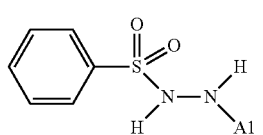
S1-86 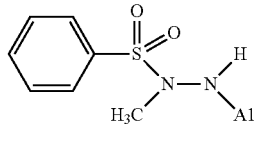
S1-87 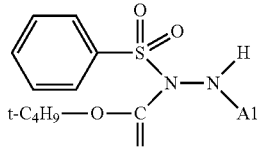
S1-88 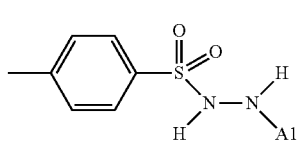
S1-89 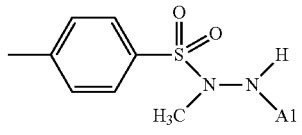
S1-90 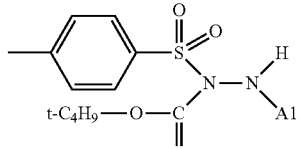
S1-91 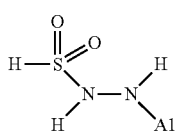

Examples in each of which in the formula (IX), one or two of the $P_1$, the $P_2$, and the $P_3$ each represent a methyl group, and the total of the numbers of carbon atoms of the $P_1$, the $P_2$, and the $P_3$ is 2 or less include S1-1, S1-2, and S1-3.

Examples in each of which in the formula (IX), at least one of the $P_1$, the $P_2$, or the $P_3$ represents a t-butoxycarbonyl group include S1-13, S1-14, and S1-15.

Examples in each of which in the formula (IX), at least one of the $P_1$, the $P_2$, or the $P_3$ represents —S(=O)$_2$—R', and the R' represents a methyl group, a 2-hydroxyethyl group, a phenyl group, or a tolyl group include S1-23, S1-31, S1-37, and S1-40.

Specific structures of the treatment agent represented by the formula (X) are represented in S2-1 to S2-40. The A1 is in conformity with the specific examples of the formula (I).

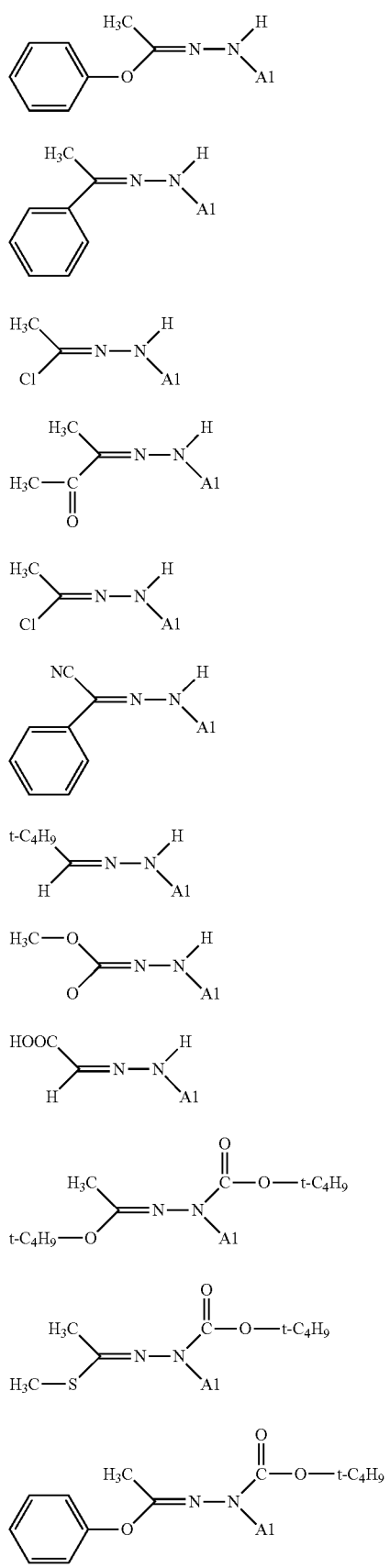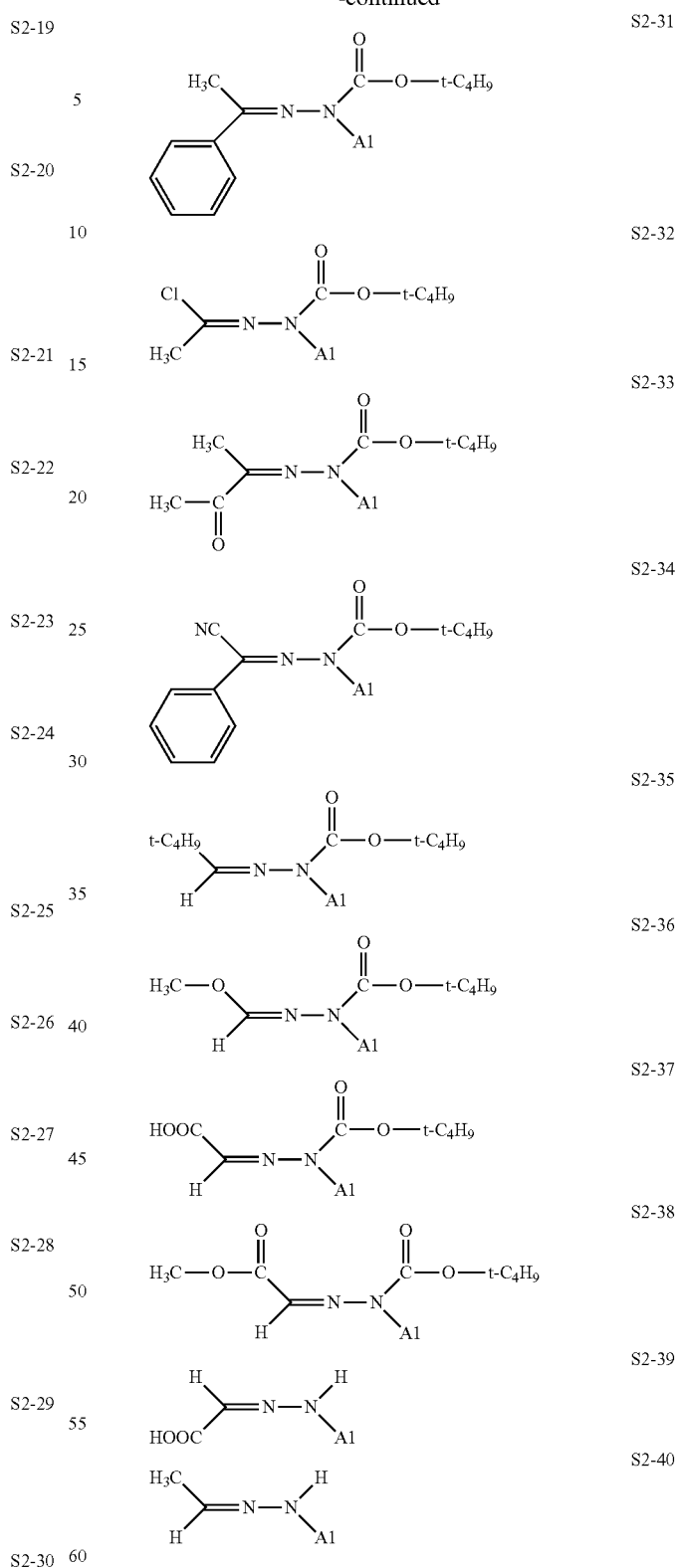
The applications of the modified graphene according to one aspect of the present disclosure produced by such method as described above are described below.
(Resin Composite)
A resin blended with the modified graphene according to one aspect of the present disclosure (hereinafter referred to as "modified graphene-resin composite") is a resin composite having imparted thereto electroconductivity or thermal conductivity inherent in a graphene, and hence may be turned into various product forms. The composite is used in the form of, for example, an electroconductive or heat conductive molded member, such as an electroconductive or heat conductive master batch, an electroconductive or heat conductive sheet, an electroconductive or heat conductive tray, or an electroconductive or heat conductive gasket, or an electrode member. In addition, it has recently been known that the blending of a resin with the graphene exhibits a function of improving the strength of the resin and a function of improving the slidability thereof. Accordingly, the composite may find applications in a strength member and a slidable member.

The modified graphene according to one aspect of the present disclosure may be used after having been blended into any one of various resins, and the kinds of the resins are not particularly limited. The reason for the foregoing is as described below. In general, the combination of a filler and a resin is limited because a problem with compatibility therebetween and a problem with the dispersion failure (aggregation) of the filler along with the problem occur. However, the substituent to be introduced into the modified graphene according to one aspect of the present disclosure can be designed in consideration of the compatibility of the modified graphene with a resin into which the modified graphene is blended, and hence the resin is not limited. Specific examples of a usable resin include the following resins: a polyethylene, a polystyrene, a vinyl acetate resin, a vinyl chloride resin, an acrylic resin, a polyacrylonitrile, a polyamide, a cellulose acetate resin, a cellulose nitrate resin, a phenol resin, an epoxy resin, a silicone resin, and a natural rubber.

When the modified graphene-resin composite according to one aspect of the present disclosure is produced, and an electroconductive sheet or a heat conductive sheet (modified graphene sheet) is produced by using the composite, a silicone resin may be suitably used. The silicone resin can be applied in a film shape and cured, and can impart thermal conductivity to the surface layer of a product by virtue of the effect of the modified graphene. Further, the use of the silicone resin provides an electroconductive sheet or heat conductive sheet having adhesive properties with various adherends. In addition, any such sheet also has excellent weatherability and excellent heat resistance.

Specific examples of the silicone resin include general silicone resins, such as a methyl silicone resin, a methyl phenyl silicone resin, and a phenyl silicone resin. Specific examples of the silicone resin also include organic resin-modified silicone resins, such as an alkyd-modified silicone resin, a polyester-modified silicone resin, an epoxy-modified silicone resin, a urethane-modified silicone resin, and an acrylic-modified silicone resin.

In addition, a two-component-type silicone resin (reactive silicone resin) may also be used. Specific examples of the reactive silicone resin include an addition curable silicone resin, a condensation curable silicone resin, a peroxide curable silicone resin, and a cationic UV-curable silicone resin. Of those, an addition curable silicone resin, which is easily available and is cured even at room temperature, is suitably used. Two compounds to be used for producing the addition curable silicone resin are a vinyl siloxane having a double bond and a hydrosiloxane. A commercial product is available as each of those compounds, and the commercial product may be used. As a vinyl-terminated polysiloxane, there may be given, for example, DMS-V31 (manufactured by AZmax Co., Ltd.) and DMS-V41 (manufactured by AZmax Co., Ltd.). As a hydrogen-terminated polysiloxane, there are given, for example, DMS-H03 (manufactured by AZmax Co., Ltd.), HMS-301 (manufactured by AZmax Co., Ltd.), and HMS-992 (manufactured by AZmax Co., Ltd.).

The weight-average molecular weight (Mw) of the resin to be used in one aspect of the present disclosure is preferably 50,000 or less. In general, when the blending amount of the filler is increased, the viscosity of the resin composite increases, or the temperature at which the filler and the resin are kneaded needs to be set to a high value. When the weight-average molecular weight (Mw) is more than 50,000, in the case where the modified graphene according to one aspect of the present disclosure is blended into the resin, for example, the following problems may occur: the viscosity of the composite becomes so high that the composite cannot be turned into a sheet; or the kneading temperature increases to such an extent that the temperature is difficult to control.

(Dispersion)

The modified graphene according to one aspect of the present disclosure may be utilized as a modified graphene dispersion in various applications. The modified graphene dispersion is obtained by subjecting the modified graphene represented by the formula (I) to a dispersion treatment in a dispersion medium.

A method for the dispersion treatment is, for example, the following method. The modified graphene represented by the formula (I), and as required, a resin are dissolved in the dispersion medium, and are sufficiently conformed to the dispersion medium while being stirred. Further, a mechanical shear force is applied to the solution with a dispersing machine, such as a ball mill, a paint shaker, a dissolver, an attritor, a sand mill, or a high-speed mill. Thus, the modified graphene represented by the formula (I) can be finely dispersed in a stable and uniform fine particulate shape.

In one aspect of the present disclosure, the amount of the modified graphene in the modified graphene dispersion is preferably from 1 part by mass to 50 parts by mass with respect to 100 parts by mass of the dispersion medium. The amount is more preferably from 2 parts by mass to 30 parts by mass, particularly preferably from 3 parts by mass to 15 parts by mass. When the content of the modified graphene is set within the range, an increase in viscosity of the modified graphene dispersion and a reduction in dispersibility of the modified graphene can be suppressed.

In the modified graphene dispersion, the modified graphene may be dispersed alone in water, or may be dispersed therein by using an emulsifying agent. Examples of the emulsifying agent include a cationic surfactant, an anionic surfactant, and a nonionic surfactant.

Examples of the cationic surfactant include the following: dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactant include: fatty acid soap, such as sodium stearate and sodium dodecanoate; and sodium dodecyl sulfate, sodium dodecyl benzene sulfate, and sodium lauryl sulfate.

Examples of the nonionic surfactant include the following: dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

As an organic solvent to be used as the dispersion medium, the following solvents are given: alcohols, such as methyl alcohol, ethyl alcohol, denatured ethyl alcohol, iso-propyl alcohol, n-butyl alcohol, isobutyl alcohol, tert-butyl alcohol, sec-butyl alcohol, tert-amyl alcohol, 3-pentanol, octyl alcohol, benzyl alcohol, and cyclohexanol; glycols, such as methyl cellosolve, ethyl cellosolve, diethylene glycol, and diethylene glycol monobutyl ether; ketones, such as acetone, methyl ethyl ketone (2-butanone), and methyl isobutyl ketone; esters, such as ethyl acetate, butyl acetate, ethyl propionate, and cellosolve acetate; hydrocarbon-based solvents, such as hexane, octane, petroleum ether, cyclohexane, benzene, toluene, and xylene; halogenated hydrocarbon-based solvents, such as carbon tetrachloride, trichloroethylene, and tetrabromoethane; ethers, such as diethyl ether, dimethyl glycol, trioxane, and tetrahydrofuran; acetals, such as methylal and diethylacetal; organic acids, such as formic acid, acetic acid, and propionic acid; and sulfur-containing and nitrogen-containing organic compounds, such as nitrobenzene, dimethylamine, monoethanolamine, pyridine, dimethyl sulfoxide, and dimethylformamide.

In addition, the use of the above-mentioned modified graphene dispersion enables the production of an electroconductive ink or paint.

According to one aspect of the present disclosure, the modified graphene that has excellent electroconductivity and excellent thermal conductivity, and that has a functional group having functionality introduced into its surface can be provided.

In addition, according to one aspect of the present disclosure, the method of producing a modified graphene that has excellent electroconductivity and excellent thermal conductivity, and that has a functional group having functionality introduced into its surface can be provided.

Further, according to one aspect of the present disclosure, the modified graphene-resin composite, the modified graphene sheet, and the modified graphene dispersion each including the modified graphene that has excellent electroconductivity and excellent thermal conductivity, and that has a functional group having functionality introduced into its surface can be provided.

EXAMPLES

The present disclosure is described in more detail below by way of Examples and Comparative Examples. The present disclosure is by no means limited to Examples below without departing from the gist of the present disclosure. "Part(s)" and "%" with regard to the description of the amounts of components are by mass, unless otherwise stated.

(Material)

Example 1-1 to Example 1-28 relate to the production of modified graphenes. Main materials used here, that is, a graphene, treatment agents, and oxidants are shown in Table 1 below.

The treatment agents are compounds each represented by the following formula (VI), and the structural formula of A1 is the same as any structure described in the section (Specific Examples of Modified Graphene). All of the treatment agents were purchased from Sumika Technoservice Corporation.

NH$_2$—NH-A1 (VI)

In addition, the names and chemical formulae of the respective oxidants are as described below.

Iron(III) phthalocyanine chloride (FePc.Cl), potassium ferrocyanide (K$_4$[Fe(CN)$_6$].3H$_2$O), iodine (I2), iron(III) chloride (FeCl$_3$), sodium periodate (NaIO$_4$), manganese dioxide (MnO$_2$), potassium permanganate (KMnO$_4$), and 35% hydrogen peroxide aqueous solution (H$_2$O$_2$). Those oxidants are all manufactured by Tokyo Chemical Industry Co., Ltd.

TABLE 1

| | | Raw material (unmodified graphene) | Treatment agent (A1 of formula (VI)) | Oxidant | Oxidation potential (V) |
|---|---|---|---|---|---|
| Example | 1-1 | xGnP-M5 | A1-22 | FePc•Cl | +0.17 |
| | 1-2 | xGnP-M5 | A1-22 | K$_4$[Fe(CN)$_6$]•3H$_2$O | +0.36 |
| | 1-3 | xGnP-M5 | A1-22 | I$_2$ | +0.49 |
| | 1-4 | xGnP-M5 | A1-22 | FeCl$_3$ | +0.77 |
| | 1-5 | xGnP-M5 | A1-22 | NaIO$_4$ | +0.98 |
| | 1-6 | xGnP-M5 | A1-22 | NaIO$_4$ (acidified with sulfuric acid) | +1.20 |
| | 1-7 | xGnP-M5 | A1-22 | MnO$_2$ | +1.28 |
| | 1-8 | xGnP-M5 | A1-22 | KMnO$_4$ (acidified with sulfuric acid) | +1.51 |
| | 1-9 | xGnP-M5 | A1-22 | H$_2$O$_2$ (acidified with sulfuric acid) | +1.77 |
| | 1-10 | xGnP-M5 | A1-7 | K$_4$[Fe(CN)$_6$]•3H$_2$O | +0.36 |
| | 1-11 | xGnP-M5 | A1-8 | K$_4$[Fe(CN)$_6$]•3H$_2$O | +0.36 |
| | 1-12 | xGnP-M5 | A1-10 | K$_4$[Fe(CN)$_6$]•3H$_2$O | +0.36 |
| | 1-13 | xGnP-M5 | A1-13 | K$_4$[Fe(CN)$_6$]•3H$_2$O | +0.36 |
| | 1-14 | xGnP-M5 | A1-14 | K$_4$[Fe(CN)$_6$]•3H$_2$O | +0.36 |
| | 1-15 | xGnP-M5 | A1-15 | K$_4$[Fe(CN)$_6$]•3H$_2$O | +0.36 |
| | 1-16 | xGnP-M5 | A1-20 | K$_4$[Fe(CN)$_6$]•3H$_2$O | +0.36 |
| | 1-17 | xGnP-M5 | A1-23 | K$_4$[Fe(CN)$_6$]•3H$_2$O | +0.36 |
| | 1-18 | xGnP-M5 | A1-26 | K$_4$[Fe(CN)$_6$]•3H$_2$O | +0.36 |
| | 1-19 | xGnP-M5 | A1-28 | K$_4$[Fe(CN)$_6$]•3H$_2$O | +0.36 |
| | 1-20 | xGnP-M5 | A1-29 | K$_4$[Fe(CN)$_6$]•3H$_2$O | +0.36 |
| | 1-21 | xGnP-M5 | A1-30 | K$_4$[Fe(CN)$_6$]•3H$_2$O | +0.36 |
| | 1-22 | xGnP-M5 | A1-64 | K$_4$[Fe(CN)$_6$]•3H$_2$O | +0.36 |
| | 1-23 | xGnP-M5 | A1-72 | K$_4$[Fe(CN)$_6$]•3H$_2$O | +0.36 |
| | 1-24 | xGnP-M5 | A1-82 | K$_4$[Fe(CN)$_6$]•3H$_2$O | +0.36 |
| | 1-25 | xGnP-M5 | A1-83 | K$_4$[Fe(CN)$_6$]•3H$_2$O | +0.36 |
| | 1-26 | xGnP-M5 | A1-85 | K$_4$[Fe(CN)$_6$]•3H$_2$O | +0.36 |
| | 1-27 | xGnP-M5 | A1-3 | K$_4$[Fe(CN)$_6$]•3H$_2$O | +0.36 |
| | 1-28 | xGnP-M5 | A1-6 | K$_4$[Fe(CN)$_6$]•3H$_2$O | +0.36 |
| Comparative Example | 1-1 | — | — | — | — |
| | 1-2 | xGnP-M5 | A1-22 | — | — |

(Production Methods)
(Production Method 1-A)

The following materials were loaded into a vessel having a volume of 400 mL (manufactured by AIMEX Co., Ltd.) and mixed.

Graphene (product name: xGnP-M5, New Metals and Chemicals Corporation, Ltd.): 18.0 g
Ion-exchanged water: 162 mL
N,N-Dimethylformamide (DMF): 18 mL
Treatment agent (Sumika Technoservice Corporation): 1.0 mmol/g
Oxidant (Tokyo Chemical Industry Co., Ltd.): 0.1 mmol/g An 8 mol/L aqueous solution of potassium hydroxide was added to the resultant liquid to adjust its pH to 3, and the mixture was stirred at a temperature of 25° C. and a number of revolutions of 2,000 rpm for 12 hours. After that, an 8 mol/L aqueous solution of potassium hydroxide was added to the resultant liquid to adjust its pH to 10. Thus, a dispersion liquid was obtained. The resultant dispersion liquid was centrifuged at a number of revolutions of 5,000 rpm for 10 minutes, and a supernatant and coarse particles were removed, followed by the purification of the supernatant liquid so that its electroconductivity became 10 μS/cm or less. Thus, a modified graphene dispersion was obtained. Next, the modified graphene dispersion was dried by a freeze-drying method.

(Production Method 1-B)

The following materials were loaded into a vessel having a volume of 400 mL (manufactured by AIMEX Co., Ltd.) and mixed.

Graphene (product name: xGnP-M5, New Metals and Chemicals Corporation, Ltd.): 18.0 g
N,N-Dimethylformamide (DMF): 180 mL
Treatment agent (Sumika Technoservice Corporation): 1.0 mmol/g
Oxidant (Tokyo Chemical Industry Co., Ltd.): 0.1 mmol/g The resultant dispersion liquid was filtered with a filter bell having arranged thereon filter paper, and the solid matter that had been filtered out was washed with DMF once and with chloroform once, followed by the addition of acetone to the washed product. Thus, a modified graphene dispersion was obtained. Next, the solvent was removed from the modified graphene dispersion with an evaporator, and the residue was dried with a vacuum dryer (50° C.).

(Method of identifying Modified Graphene)

The identification of each of the modified graphenes thus produced, that is, the determination of the amount of a substituent (hereinafter sometimes described as "modification amount") thereof is described below. The modification amount was calculated by using a composition ratio, which had been obtained from the composition amount of each element in the unmodified graphene (raw material) or the modified graphene determined by X-ray photoelectron measurement with Quantera SXM (manufactured by ULVAC-PHI, Incorporated), and the following calculation equation 1. An excitation X-ray is a monochromatic Al Kα 1,2 ray (1,486.6 eV), the diameter of the X-ray is 100 am, and the angle at which a photoelectron escapes is 45°.

Modification amount (mmol/g)=(Ratio of element that forms A1 and is increased after modification-Ratio of unmodified graphene element)/(Molecular weight of element that forms A1 and is increased after modification×Number of moles of element increased in A1)    Calculation equation 1

To give an example, the element composition amount of a modified graphene in which the structure of the A1 was A1-22 was a value shown in the lower row of Table 2 below. Meanwhile, the element composition amount of the graphene used as a raw material (xGnP-M5 (New Metals and Chemicals Corporation, Ltd.)) was a value shown in the upper row of Table 2 below. In this case, the modification amount of A1-22 with respect to 1 g of the modified graphene was estimated to be 0.219 mmol/g from the calculation equation 1.

TABLE 2

| | C1s | O1s |
|---|---|---|
| xGnP-M5 | 99.0 | 1.0 |
| Modified graphene including A1-22 | 98.3 | 1.7 |

(Evaluation of Defect Concentration of Modified Graphene by Raman Spectroscopy)

Raman spectroscopy was performed with the following apparatus under the following conditions.

Measuring apparatus: ARaman microscope (NRS-4100 manufactured by JASCO Corporation)

Measurement conditions: A laser beam having a wavelength of 532 nm was used, the intensity of the laser beam was 0.3 mW, the magnification of an objective lens was 20, an exposure time was 60 seconds, and the number of scans was 2 (resolution=7 cm$^{-1}$).

When a graphene structure is present, a G band (around 1,590 cm$^{-1}$) derived from a graphite structure (sp$^2$ bond) and a D band (around 1,350 cm$^{-1}$) derived from a defect are observed. As the G band has a higher intensity and a sharper shape, and the D band has a lower intensity, the graphene can be said to have a smaller number of defects. The defect concentration of the graphene was evaluated by using the following equation.

$G/D$ ratio=$g/d$ g: The intensity of the G band
d: The intensity of the D band
[Evaluation Criteria]
Rank A . . . 0.95≤g/d
Rank B . . . 0.80≤g/d<0.95
Rank C . . . g/d<0.80

Example 1-1 to Example 1-9, Example 1-17, Example 1-18, and Example 1-22

Modified graphenes 1-1 to 1-9, a modified graphene 1-17, a modified graphene 1-18, and a modified graphene 1-22 were each produced in accordance with Production Method 1-A by using the graphene, the treatment agent, and the oxidant shown in Table 1.

Next, the element composition amounts of the modified graphenes were determined by X-ray photoelectron measurement, and the modification amounts thereof were estimated from the calculation equation 1 and shown in Table 3. Further, the g/d values of the modified graphenes thus produced were determined by Raman spectroscopy, evaluated based on the evaluation criteria, and shown in Table 3.

Example 1-10 to Example 1-16, Example 1-19 to Example 1-21, and Example 1-23 to Example 1-28

Modified graphenes 1-10 to 1-16, modified graphenes 1-19 to 1-21, and modified graphenes 1-23 to 1-28 were each produced in accordance with Production Method 1-B by using the graphene, the treatment agent, and the oxidant shown in Table 1.

Next, the element composition amounts of the modified graphenes were determined by X-ray photoelectron measurement, and the modification amounts thereof were estimated from the calculation equation 1 and shown in Table 3. Further, the g/d values of the modified graphenes thus produced were determined by Raman spectroscopy, evaluated based on the evaluation criteria, and shown in Table 3.

Comparative Example 1-1

A graphene oxide (product name: GO, New Metals and Chemicals Corporation, Ltd.) was used as a comparative compound 1-1.

The g/d value of the produced graphene oxide was determined by Raman spectroscopy, evaluated based on the evaluation criteria, and shown in Table 3.

Comparative Example 1-2

A modified graphene obtained by using 4-aminobenzoic acid as a treatment agent in accordance with the following production method described in Japanese Patent No. 3980637 was used as a comparative compound 1-2.

The following materials were loaded into a vessel having a volume of 400 mL (manufactured by AIMEX Co., Ltd.) and mixed.
Graphene (product name: xGnP-M5, manufactured by New Metals and Chemicals Corporation, Ltd.): 18.0 g
Ion-exchanged water: 162 mL
4-Aminobenzoic acid (manufactured by Tokyo Chemical Industry Co., Ltd.): 1.0 mmol/g
Sodium nitrite (manufactured by Tokyo Chemical Industry Co., Ltd.): 1.0 mmol/g The mixture was stirred at a temperature of 25° C. and a number of revolutions of 2,000 rpm for 12 hours. After that, an 8 mol/L aqueous solution of potassium hydroxide was added to the resultant liquid to adjust its pH to 10. Thus, a dispersion liquid was obtained. The resultant dispersion liquid was centrifuged at a number of revolutions of 5,000 rpm for 10 minutes, and a supernatant and coarse particles were removed, followed by the purification of the supernatant liquid so that its electroconductivity became 10 μS/cm or less. Thus, a modified graphene dispersion was obtained. Next, the modified graphene dispersion was dried by a freeze-drying method.

The element composition amount of the modified graphene was determined by X-ray photoelectron measurement, and the modification amount thereof was estimated from the calculation equation 1 and shown in Table 3. Further, the g/d value of the modified graphene thus produced was determined by Raman spectroscopy, evaluated based on the evaluation criteria, and shown in Table 3.

(Method of producing Resin Composite of Modified Graphene)

A resin sheet blended with any one of the modified graphenes produced in the foregoing was produced by using any one of Production Method 1-1, Production Method 1-2, and Production Method 1-3 described below. Further, the electroconductivity evaluation and thermal conductivity evaluation of the resultant sheet were performed.

In addition, a resin sheet blended with the graphene oxide (the comparative compound 1-1) and a resin sheet blended with the modified graphene (the comparative compound 1-2) produced by the production method described in Japanese Patent No. 3980637 were produced, and were subjected to the same evaluations.

Production Method 1-1, Production Method 1-2, or Production Method 1-3 described above is described below. Production Method 1-1 is a method relating to a sheet using a silicone resin, Production Method 1-2 is a method relating to a sheet using a urethane resin, and Production Method 1-3 is a method relating to a sheet using a polyimide.

(Production Method 1-1)

100 Parts of a vinyl-terminated polysiloxane DMS-V31 (weight-average molecular weight (Mw): 28,000, AZmax Co., Ltd.), 5 parts of a hydrogen-terminated polysiloxane HMS-301 (AZmax Co., Ltd.), and 60 parts of a modified graphene (or a comparative compound) were mixed with a spatula.

Next, the mixture was kneaded with a planetary mixer (NR-50, manufactured by Thinky Corporation) for 2 minutes, and was defoamed therewith for 1 minute. 0.8 Part of a platinum catalyst was added to the defoamed product, and was kneaded thereinto with a spatula. Next, the mixture was kneaded with a planetary mixer (NR-50, manufactured by Thinky Corporation) for 2 minutes, and was defoamed therewith for 1 minute. The resultant mixture was applied onto a metal plate with a bar coater, and was left at rest in

TABLE 3

| | | Modified graphene/comparative compound | | | | |
|---|---|---|---|---|---|---|
| | No. | | Structure | Modification amount (mmol/g) | g/d value | g/d rank |
| Example | 1-1 | Modified graphene 1-1 | A1-22 | 0.175 | 1.1 | A |
| | 1-2 | Modified graphene 1-2 | A1-22 | 0.177 | 1.1 | A |
| | 1-3 | Modified graphene 1-3 | A1-22 | 0.199 | 10.7 | A |
| | 1-4 | Modified graphene 1-4 | A1-22 | 0.204 | 1.1 | A |
| | 1-5 | Modified graphene 1-5 | A1-22 | 0.218 | 1.1 | A |
| | 1-6 | Modified graphene 1-6 | A1-22 | 0.209 | 1.0 | A |
| | 1-7 | Modified graphene 1-7 | A1-22 | 0.230 | 1.0 | A |
| | 1-8 | Modified graphene 1-8 | A1-22 | 0.255 | 1.0 | A |
| | 1-9 | Modified graphene 1-9 | A1-22 | 0.145 | 1.0 | A |
| | 1-10 | Modified graphene 1-10 | A1-7 | 0.158 | 1.1 | A |
| | 1-11 | Modified graphene 1-11 | A1-8 | 0.165 | 1.1 | A |
| | 1-12 | Modified graphene 1-12 | A1-10 | 0.159 | 1.1 | A |
| | 1-13 | Modified graphene 1-13 | A1-13 | 0.144 | 1.1 | A |
| | 1-14 | Modified graphene 1-14 | A1-14 | 0.163 | 2.0 | A |
| | 1-15 | Modified graphene 1-15 | A1-15 | 0.166 | 1.1 | A |
| | 1-16 | Modified graphene 1-16 | A1-20 | 0.171 | 1.1 | A |
| | 1-17 | Modified graphene 1-17 | A1-23 | 0.183 | 1.1 | A |
| | 1-18 | Modified graphene 1-18 | A1-26 | 0.177 | 1.1 | A |
| | 1-19 | Modified graphene 1-19 | A1-28 | 0.169 | 1.1 | A |
| | 1-20 | Modified graphene 1-20 | A1-29 | 0.188 | 1.0 | A |
| | 1-21 | Modified graphene 1-21 | A1-30 | 0.174 | 1.1 | A |
| | 1-22 | Modified graphene 1-22 | A1-64 | 0.153 | 1.1 | A |
| | 1-23 | Modified graphene 1-23 | A1-72 | 0.191 | 1.1 | A |
| | 1-24 | Modified graphene 1-24 | A1-82 | 0.167 | 1.1 | A |
| | 1-25 | Modified graphene 1-25 | A1-83 | 0.196 | 2.0 | A |
| | 1-26 | Modified graphene 1-26 | A1-85 | 0.192 | 1.1 | A |
| | 1-27 | Modified graphene 1-27 | A1-3 | 0.175 | 1.1 | A |
| | 1-28 | Modified graphene 1-28 | A1-6 | 0.184 | 1.1 | A |
| Comparative Example | 1-1 | Comparative compound 1-1 | — | — | 0.8 | C |
| | 1-2 | Comparative compound 1-2 | A1-22 | 0.171 | 0.9 | B | a thermostatic chamber at 100° C. for 2 hours to be cured. Thus, the following silicone resin sheet was obtained:
Silicone resin sheet
Thickness: 200±10 μm
The blending amount of the modified graphene (or the comparative compound): 20 vol %
provided that the blending amount was calculated by defining the density of the modified graphene as 2.2 g/cm$^3$ and defining the density of any other material as 0.97 g/cm$^3$.

(Production Method 1-2)

The following materials were mixed, and the mixture was stirred for 1 hour while an ultrasonic wave was applied thereto. Thus, a dispersion liquid was prepared.
A polyurethane UR-4800 serving as a binder resin (weight-average molecular weight (Mw): 4,800, Toyobo Co., Ltd.) 100 parts
A modified graphene (or a comparative compound) 43 parts
An arbitrary amount of tetrahydrofuran (THF, manufactured by Kishida Chemical Co., Ltd.)

The resultant mixture was applied onto a metal plate with a bar coater, and was dried in a thermostatic dryer at 40° C. Next, the dried body was peeled from the metal plate, and was heated and pressurized with a small heat pressing machine (manufactured by AS ONE Corporation) at 150° C. and 0.5 kgf/m$^2$ for 3 minutes. Thus, the following urethane resin sheet was obtained:
Urethane resin sheet
Thickness: 200±10 μm
The blending amount of the modified graphene (or the comparative compound): 20 vol %
provided that the blending amount was calculated by defining the density of the modified graphene as 2.2 g/cm$^3$ and defining the density of the urethane resin as 1.28 g/cm$^3$.

(Production Method 1-3)

100 Parts of a polyimide precursor U-VARNISH-S (solid content concentration: 20%, N-methylpyrrolidone content: 80%, Ube Industries, Ltd.) and 5.2 parts of a modified graphene (or a comparative compound) were mixed with a spatula.

Next, the mixture was kneaded with a planetary mixer (NR-50, manufactured by Thinky Corporation) for 2 minutes, and was defoamed therewith for 1 minute. The resultant mixture was applied onto a metal plate with a bar coater, and was left at rest in a thermostatic chamber at 100° C. for 2 hours so that its solvent was removed. Further, the residue was dried under a reduced pressure of 0.05 MPa in a vacuum dryer at 100° C. Further, the dried product was calcined in a muffle furnace at 290° C. for 30 minutes and at 350° C. for 30 minutes. Thus, the following polyimide sheet was obtained:
Polyimide sheet
Thickness: 85±3 μm
The blending amount of the modified graphene (or the comparative compound): 15 vol %
provided that the blending amount was calculated by defining the density of the modified graphene as 2.2 g/cm$^3$ and defining the density of the polyimide as 1.47 g/cm$^3$.

Example 1-29 to Example 1-56

Modified graphene-blended silicone resin sheets were produced by: using the modified graphenes 1-1 to 1-28 shown in Table 3; and using Production Method 1-1 described above. Further, the sheets were each cut into a predetermined sample shape, and were each subjected to an electroconductivity evaluation and a thermal conductivity evaluation. The results are shown in Table 4.

Example 1-57 and Example 1-58

Modified graphene-blended urethane resin sheets were produced by: using the modified graphene 1-2 and the modified graphene 1-8 shown in Table 3; and using Production Method 1-2 described above. Further, the sheets were each cut into a predetermined sample shape, and were each subjected to an electroconductivity evaluation and a thermal conductivity evaluation. The results are shown in Table 4.

Example 1-59

A modified graphene-blended silicone resin sheet was produced by: using a vinyl-terminated polysiloxane DMS-V41 (weight-average molecular weight (Mw): 50,000, AZmax Co., Ltd.) instead of the vinyl-terminated polysiloxane DMS-V31; using the modified graphene 1-2; and using Production Method 1-1 described above. Further, the sheet was cut into a predetermined sample shape, and was subjected to an electroconductivity evaluation and a thermal conductivity evaluation. The results are shown in Table 4.

Example 1-60

A modified graphene-blended silicone resin sheet was produced by: using a vinyl-terminated polysiloxane DMS-V46 (weight-average molecular weight (Mw): 117,000, AZmax Co., Ltd.) instead of the vinyl-terminated polysiloxane DMS-V31; using the modified graphene 1-2; and using Production Method 1-1 described above. Further, the sheet was cut into a predetermined sample shape, and was subjected to an electroconductivity evaluation and a thermal conductivity evaluation. The results are shown in Table 4.

Comparative Example 1-3

A graphene oxide-blended silicone resin sheet was produced by using the graphene oxide (product name: GO, New Metals and Chemicals Corporation, Ltd.) and in conformity with Production Method 1-1 described above. Further, the sheet was cut into a predetermined sample shape, and was subjected to an electroconductivity evaluation and a thermal conductivity evaluation. The results are shown in Table 4.

Comparative Example 1-4

A graphene oxide-blended silicone resin sheet was produced by: using the modified graphene (the comparative compound 1-2) produced by using the production method described in Japanese Patent No. 3980637; and using Production Method 1-1 described above. Further, the sheet was cut into a predetermined sample shape, and was subjected to an electroconductivity evaluation and a thermal conductivity evaluation. The results are shown in Table 4.

(Evaluations)

The electroconductivity evaluations and thermal conductivity evaluations of the resin sheets produced in the foregoing were performed by the following methods, and the sheets were evaluated in accordance with the following evaluation criteria.

(Electroconductivity Evaluation)

An electroconductivity evaluation was performed based on the surface electrical resistivity (kΩ/□) of a resin sheet sample. The surface electrical resistivity was measured in conformity with JIS K 7194 "Testing method for resistivity of conductive plastics with a four-point probe array," and the sample was classified into any one of a rank A to a rank C as described below by using the measured value. It has been generally known that the surface electrical resistivity of an electroconductive member is less than $1×10^5 Ω/□$, and a member having a surface electrical resistivity of $1×10^5 Ω/□$ or more is a static electricity diffusive member ($1×10^5 Ω/□$ or more and less than $1×10^9 Ω/□$) or an antistatic member ($1×10^9 Ω/□$ or more and less than $1×10^{12} Ω/□$). Accordingly, in one aspect of the present disclosure, only a resin sheet sample classified into a rank acceptable as an electroconductive member, that is, the rank A was defined as an acceptable rank.

[Evaluation Criteria]
Rank A . . . 10 kΩ/□≤surface electrical resistivity<100 kΩ/□
Rank B . . . 100 kΩ/□≤surface electrical resistivity<1,000 kΩ/□
Rank C . . . 1,000 kΩ/□≤surface electrical resistivity (Thermal Conductivity Evaluation)

A thermal conductivity evaluation was performed based on the thermal conductivity of a resin sheet sample (having a thickness of 200±10 μm) in its thickness direction.

First, the produced resin sheets were each cut into a size measuring 6 mm long by 11 mm wide. The sheet was used as a resin sheet sample, and its thermal diffusivity a in its thickness direction was measured with a temperature wave analyzer (manufactured by ULVAC-RIKO, Inc., FTC-1). The thermal conductivity λ of the sample was calculated from the equation "$λ=α×Cp×ρ$" by multiplying the thermal diffusivity a determined in the measurement by the specific heat Cp (weight fraction average) and density ρ (volume fraction average) thereof. The density was measured by using a submerged replacement method, and the specific heat was measured with a differential scanning calorimeter (PYRIS Diamond DSC-7, DSC, manufactured by PerkinElmer). The specific heat Cp and the density ρ needed for the calculation are as described below.

The sheet was classified into any one of a rank A to a rank C as described below by using the resultant value of the thermal conductivity. A member having a thermal conductivity of 1 W/m·K or more in its thickness direction is generally recognized as a high-performance heat conductive member. Accordingly, only a resin sheet sample classified into the rank A was defined as an acceptable rank.

[Evaluation Criteria]
Rank A . . . 1 W/m·K≤thermal conductivity
Rank B . . . 0.5 W/m·K≤thermal conductivity<1 W/m·K
Rank C . . . thermal conductivity<0.5 W/m·K

[Densities and Specific Heats of Respective Materials Used in Calculation]

The density ρ of each of the silicone resins: 0.97 g/cm³
The density ρ of the urethane resin: 1.28 g/cm³
The density ρ of each of the modified graphenes and the comparative compound 1-2: 2.2 g/cm³
The density ρ of the graphene oxide: 2.1 g/cm³
The specific heat Cp of each of the silicone resins: 1,600 J/kgK
The specific heat Cp of the urethane resin: 1,900 J/kgK
The specific heat Cp of each of the modified graphenes and the comparative compound 1-2: 710 J/kgK
The specific heat Cp of the graphene oxide: 700 J/kgK

TABLE 4

|  |  | Production method | Number of modified graphene or comparative compound | Weight-average molecular weight of resin | Filler amount (vol %) | Surface electrical resistivity (KΩ/□) | Electroconductivity rank | Thermal conductivity (W/m · K) | Thermal conductivity rank |
|---|---|---|---|---|---|---|---|---|---|
| Example | 1-29 | 1-1 | Modified graphene 1-1 | 28,000 | 20 | 45 | A | 1.5 | A |
|  | 1-30 | 1-1 | Modified graphene 1-2 | 28,000 | 20 | 44 | A | 1.5 | A |
|  | 1-31 | 1-1 | Modified graphene 1-3 | 28,000 | 20 | 32 | A | 1.6 | A |
|  | 1-32 | 1-1 | Modified graphene 1-4 | 28,000 | 20 | 38 | A | 1.5 | A |
|  | 1-33 | 1-1 | Modified graphene 1-5 | 28,000 | 20 | 40 | A | 1.5 | A |
|  | 1-34 | 1-1 | Modified graphene 1-6 | 28,000 | 20 | 37 | A | 1.6 | A |
|  | 1-35 | 1-1 | Modified graphene 1-7 | 28,000 | 20 | 44 | A | 1.4 | A |
|  | 1-36 | 1-1 | Modified graphene 1-8 | 28,000 | 20 | 25 | A | 1.5 | A |
|  | 1-37 | 1-1 | Modified graphene 1-9 | 28,000 | 20 | 41 | A | 1.5 | A |
|  | 1-38 | 1-1 | Modified graphene 1-10 | 28,000 | 20 | 55 | A | 1.3 | A |
|  | 1-39 | 1-1 | Modified graphene 1-11 | 28,000 | 20 | 40 | A | 1.4 | A |
|  | 1-40 | 1-1 | Modified graphene 1-12 | 28,000 | 20 | 32 | A | 1.5 | A |
|  | 1-41 | 1-1 | Modified graphene 1-13 | 28,000 | 20 | 19 | A | 1.7 | A |
|  | 1-42 | 1-1 | Modified graphene 1-14 | 28,000 | 20 | 28 | A | 1.6 | A |
|  | 1-43 | 1-1 | Modified graphene 1-15 | 28,000 | 20 | 31 | A | 1.4 | A |
|  | 1-44 | 1-1 | Modified graphene 1-16 | 28,000 | 20 | 42 | A | 1.5 | A |
|  | 1-45 | 1-1 | Modified graphene 1-17 | 28,000 | 20 | 39 | A | 1.2 | A |
|  | 1-46 | 1-1 | Modified graphene 1-18 | 28,000 | 20 | 35 | A | 1.5 | A |
|  | 1-47 | 1-1 | Modified graphene 1-19 | 28,000 | 20 | 32 | A | 1.5 | A |
|  | 1-48 | 1-1 | Modified graphene 1-20 | 28,000 | 20 | 48 | A | 1.6 | A |
|  | 1-49 | 1-1 | Modified graphene 1-21 | 28,000 | 20 | 53 | A | 1.4 | A |
|  | 1-50 | 1-1 | Modified graphene 1-22 | 28,000 | 20 | 22 | A | 1.5 | A |
|  | 1-51 | 1-1 | Modified graphene 1-23 | 28,000 | 20 | 41 | A | 1.5 | A |
|  | 1-52 | 1-1 | Modified graphene 1-24 | 28,000 | 20 | 38 | A | 1.3 | A |
|  | 1-53 | 1-1 | Modified graphene 1-25 | 28,000 | 20 | 28 | A | 1.4 | A |
|  | 1-54 | 1-1 | Modified graphene 1-26 | 28,000 | 20 | 39 | A | 1.5 | A |
|  | 1-55 | 1-1 | Modified graphene 1-27 | 28,000 | 20 | 54 | A | 1.7 | A |
|  | 1-56 | 1-1 | Modified graphene 1-28 | 28,000 | 20 | 39 | A | 1.6 | A |
|  | 1-57 | 1-2 | Modified graphene 1-2 | 28,000 | 20 | 40 | A | 1.4 | A |

TABLE 4-continued

| | | Production method | Number of modified graphene or comparative compound | Weight-average molecular weight of resin | Filler amount (vol %) | Surface electrical resistivity (KΩ/□) | Electroconductivity rank | Thermal conductivity (W/m · K) | Thermal conductivity rank |
|---|---|---|---|---|---|---|---|---|---|
| | 1-58 | 1-2 | Modified graphene 1-8 | 28,000 | 20 | 25 | A | 1.4 | A |
| | 1-59 | 1-1 | Modified graphene 1-2 | 50,000 | 20 | 77 | A | 1.2 | A |
| | 1-60 | 1-1 | Modified graphene 1-2 | 117,000 | 20 | 98 | A | 1.1 | A |
| Comparative Example | 1-1 | 1-1 | Comparative compound 1 | 28,000 | 20 | 3,277 | C | 0.3 | C |
| Example | 1-2 | 1-1 | Comparative compound 2 | 28,000 | 20 | 118 | B | 0.7 | B |

Example 1-61 and Example 1-62

Modified graphene-blended polyimide sheets were each produced by: using the modified graphene 1-3 or the modified graphene 1-17 shown in Table 3; and using Production Method 1-3 described above. Further, the sheets were each cut into a predetermined sample shape, and were each subjected to a thermal conductivity evaluation. The results are shown in Table 5.

Comparative Example 1-5

An unmodified graphene-blended polyimide sheet was produced by: using an unmodified graphene xGnP-M5 (New Metals and Chemicals Corporation, Ltd.); and using Production Method 1-3 described above. Further, the sheet was cut into a predetermined sample shape, and was subjected to a thermal conductivity evaluation. The results are shown in Table 5.

Comparative Example 1-6

A graphene oxide-blended polyimide sheet was produced by: using the comparative compound 1-1; and using Production Method 1-3 described above. Further, the sheet was cut into a predetermined sample shape, and was subjected to a thermal conductivity evaluation. The results are shown in Table 5.

Comparative Example 1-7

A comparative compound 1-2-blended polyimide sheet was produced by: using the comparative compound 1-2; and using Production Method 1-3 described above. Further, the sheet was cut into a predetermined sample shape, and was subjected to a thermal conductivity evaluation. The results are shown in Table 5.

[Thermal Conductivity Evaluation of Polyimide Sheet]

The thermal conductivities of the polyimide sheets blended with the modified graphenes according to one aspect of the present disclosure, and the polyimide sheets each blended with the comparative compound 1-1 or the comparative compound 1-2 were each evaluated based on the thermal conductivity of a sheet sample (having a thickness of 85±3 μm) in its thickness direction.

First, the produced resin sheets were each cut into a size measuring 6 mm long by 11 mm wide. The sheet was used as a sheet sample, and its thermal diffusivity a in its thickness direction was measured with a temperature wave analyzer (manufactured by ULVAC-RIKO, Inc., FTC-1). The thermal conductivity λ of the sample was calculated from the equation "$\lambda = a \times Cp \times \rho$" by multiplying the thermal diffusivity a determined in the measurement by the specific heat Cp (weight fraction average) and density ρ (volume fraction average) thereof. The density was measured by using a submerged replacement method, and the specific heat was measured with a differential scanning calorimeter (PYRIS Diamond DSC-7, DSC, manufactured by PerkinElmer). The specific heat Cp and the density ρ needed for the calculation are as described below.

The sheet was classified into any one of a rank A to a rank C as described below by using the resultant value of the thermal conductivity. A member having a thermal conductivity of 1 W/m·K or more in its thickness direction is generally recognized as a high-performance heat conductive member. Accordingly, only a sheet sample classified into the rank A was defined as an acceptable rank.

[Evaluation Ranks]
Rank A . . . 0.6 W/m·K≤thermal conductivity
Rank B . . . 0.3 W/m·K≤thermal conductivity<0.6 W/m·K
Rank C . . . thermal conductivity<0.3 W/m·K

[Densities and Specific Heats of Respective Materials Used in Calculation]
The density ρ of the polyimide: 1.47 g/cm³
The density ρ of each of the modified graphenes and the comparative compound 1-2: 2.2 g/cm³
The density ρ of the graphene oxide: 2.1 g/cm³
The specific heat Cp of the polyimide resin: 1,130 J/kgK
The specific heat Cp of each of the modified graphenes and the comparative compound 1-2: 710 J/kgK
The specific heat Cp of the graphene oxide: 700 J/kgK
The foregoing results are shown in Table 5.

TABLE 5

| | | Production method | Filler | Filler amount (vol %) | Thermal conductivity (W/m · K) | Thermal conductivity evaluation rank |
|---|---|---|---|---|---|---|
| Example | 1-61 | 3 | Modified graphene 1-3 | 15 | 0.8 | A |
| | 1-62 | 3 | Modified graphene 1-17 | 15 | 1 | A |

TABLE 5-continued

|  | | Production method | Filler | Filler amount (vol %) | Thermal conductivity (W/m · K) | Thermal conductivity evaluation rank |
|---|---|---|---|---|---|---|
| Comparative Example | 1-5 | 3 | Unmodified graphene xGnP-M5 | 15 | 0.5 | B |
|  | 1-6 | 3 | Comparative compound 1-1 | 15 | 0.3 | C |
|  | 1-7 | 3 | Comparative compound 1-2 | 15 | 0.5 | C |

It was able to be confirmed that the polyimide sheets blended with the modified graphenes according to one aspect of the present disclosure showed thermal conductivities higher than those of the polyimide sheets of Comparative Examples. What is more interesting is that even when the modified graphene-blended polyimide sheets and the unmodified graphene-blended polyimide sheet were compared to each other, the modified graphene-blended polyimide sheets showed thermal conductivities higher than that of the other. Although a reason for the foregoing is unclear, in consideration of the fact that in a tensile test (performed with an Instron universal tester) in conformity with K 7161 of JIS Standard, while the tensile strength (25° C.) of each of the modified graphene-blended polyimide sheets was 260 MPa, the tensile strength (25° C.) of the unmodified graphene-blended polyimide sheet was 150 MPa, there is a possibility that a carboxylic acid on the surface of each of the modified graphenes and a reactive amine in the varnish that was a polyimide precursor were bonded to each other to exhibit an effect of improving the degree of adhesiveness between the graphene and the resin or forming the network of the graphene, thereby leading to a high thermal conductivity.

(Production of Modified Graphene Dispersion)

A modified graphene dispersion according to one aspect of the present disclosure and a comparative graphene dispersion were each produced by a method described below.

Example 1-63

100 Parts of the modified graphene 1-12 shown in Table 3, 350 parts of toluene, 350 parts of ethyl acetate, and 300 parts of 2-butanone serving as dispersion media, and 750 parts of glass beads (each having a diameter of 1 mm) were mixed, and the mixture was subjected to dispersion with an attritor (Nippon Coke & Engineering Co., Ltd.) for 3 hours. After that, the resultant was filtered with a mesh to provide a modified graphene dispersion according to one aspect of the present disclosure.

Example 1-64

A modified graphene dispersion was obtained by the same operation as that of Example 1-63 except that the modified graphene 1-12 was changed to the modified graphene 1-21.

Example 1-65

A modified graphene dispersion was obtained by the same operation as that of Example 1-63 except that the modified graphene 1-12 was changed to the modified graphene 1-23.

Example 1-66

A modified graphene dispersion was obtained by the same operation as that of Example 1-63 except that the modified graphene 1-12 was changed to the modified graphene 1-25.

Comparative Example 1-8

A comparative graphene dispersion was obtained by the same operation as that of Example 1-63 except that the modified graphene 1-12 was changed to the comparative compound 1-1 (graphene oxide, product name: GO, New Metals and Chemicals Corporation, Ltd.).

Comparative Example 1-9

A comparative graphene dispersion was obtained by the same operation as that of Example 1-63 except that the modified graphene 1-12 was changed to the modified graphene (the comparative compound 1-2) produced in conformity with the production method described in Japanese Patent No. 3980637.

Comparative Example 1-10

A comparative graphene dispersion was obtained by the same operation as that of Example 1-63 except that the modified graphene 1-12 was changed to the comparative compound 1-3 (untreated graphene, product name: xGnP-M5, New Metals and Chemicals Corporation, Ltd.).

(Evaluation)

(Sample Production)

Each of the modified graphene dispersions and the comparative graphene dispersions was applied onto a PET film by a bar coating method (number of the annealing wire of a bar coater: No. 10), and was dried under reduced pressure overnight. Thus, samples were produced. The surface resistivities of the resultant samples were measured by the method described in the foregoing, and were evaluated by the following criteria. The results are shown in Table 6.

[Evaluation Criteria]

Rank A . . . 10 KΩ/□≤surface electrical resistivity<100 KΩ/□

Rank B . . . 100 KΩ/□≤surface electrical resistivity<1,000 KΩ/□

Rank C . . . 1,000 KΩ/□≤surface electrical resistivity

TABLE 6

| | | | Surface electrical resistivity (kΩ/□) | Evaluation rank |
|---|---|---|---|---|
| Example | 1-63 | Modified graphene No. 1-12 | 64 | A |
| | 1-64 | Modified graphene No. 1-21 | 38 | A |
| | 1-65 | Modified graphene No. 1-23 | 71 | A |
| | 1-66 | Modified graphene No. 1-25 | 68 | A |
| Comparative Example | 1-8 | Comparative compound 1-1 | 4,276 | C |
| | 1-9 | Comparative compound 1-2 | 329 | B |
| | 1-10 | Comparative compound 1-3 | 107 | B |

<Production of Modified Graphene by Method According to Second Embodiment>

The term "mmol/g" in the following description concerning a production method means the number of millimoles per 1.0 g of a modified graphene.

Example 2-1

A modified graphene represented by the formula A1-22 was synthesized as described below.

The following materials were loaded into a vessel having a volume of 400 mL (manufactured by AIMEX Co., Ltd.) and mixed.

Graphene (product name: xGnP-M5, manufactured by New Metals and Chemicals Corporation, Ltd.): 18.0 g
Ion-exchanged water: 162 mL
N,N-Dimethylformamide (DMF): 18 mL
Treatment agent S1-2 (manufactured by Sumika Technoservice Corporation): 1.0 mmol/g An 8 mol/L aqueous solution of potassium hydroxide was added to the resultant liquid to adjust its pH to 3, and the mixture was stirred at a temperature of 25° C. and a number of revolutions of 2,000 rpm for 12 hours. After that, an 8 mol/L aqueous solution of potassium hydroxide was added to the resultant liquid to adjust its pH to 10. Thus, a dispersion liquid was obtained. The resultant dispersion liquid was centrifuged at a number of revolutions of 5,000 rpm for 10 minutes, and a supernatant and coarse particles were removed, followed by the purification of the supernatant liquid so that its electroconductivity became 10 μS/cm or less. Thus, a modified graphene 2-1 having a structure represented by the formula A1-22 was obtained.

The modified graphene 2-1 was dried by a freeze-drying method, and the X-ray photoelectron spectrometry of the resultant powder was performed, followed by the estimation of its modification amount in accordance with the calculation equation 1.

The modification amount of the modified graphene: 0.125 mmol/g

The element composition amount of the graphene (unmodified graphene) used as a raw material: A value shown in the upper row of Table 7

The element composition amount of the modified graphene: A value shown in the lower row of Table 7

TABLE 7

| | C1s | N1s | O1s |
|---|---|---|---|
| xGnP-M5 (unmodified graphene) | 99.0 | 0.0 | 1.0 |
| Modified graphene 2-1 | 94.4 | 0.0 | 5.0 |

Examples 2-2 to 2-48

Modified graphenes 2-2 to 2-48 were each obtained in the same manner as in Example 2-1 except that the treatment agent was changed to any one of treatment agents shown in Table 8A (each manufactured by Sumika Technoservice Corporation).

The structures and modification amounts of the resultant modified graphenes 2-2 to 2-48 are shown in Table 8A.

Comparative Example 2-1

A graphene oxide (product name: GO, manufactured by New Metals and Chemicals Corporation, Ltd.) was used as a comparative compound 2-1.

Comparative Example 2-2

A modified graphene obtained by using 4-aminobenzoic acid as a treatment agent in accordance with the method described in Japanese Patent No. 3980637 was used as a comparative compound 2-2.

[Evaluation of Defect Concentration of Modified Graphene]

Raman spectroscopy was performed with the following apparatus under the following conditions.

Measuring apparatus: ARaman microscope (NRS-4100 manufactured by JASCO Corporation)

Measurement conditions: A laser beam having a wavelength of 532 nm was used, the intensity of the laser beam was 0.3 mW, the magnification of an objective lens was 20, an exposure time was 60 seconds, and the number of scans was 2 (resolution=7 cm 1).

When a graphene structure is present, a G band (around 1,590 cm$^{-1}$) derived from a graphite structure (sp$^2$ bond) and a D band (around 1,350 cm$^{-1}$) derived from a defect are observed. As the G band has a higher intensity and a sharper shape, and the D band has a lower intensity, the graphene can be said to have a smaller number of defects. The defect concentration of the graphene was evaluated by using the following equation.

G/D ratio=g/d g: The intensity of the G band
d: The intensity of the D band
Evaluation criteria are as described below.
Rank A: 0.95≤g/d
Rank B: 0.80≤g/d<0.95
Rank C: g/d<0.80

The foregoing results are shown in Tables 8A and 8B.

TABLE 8A

| Example No. | Modified graphene No. | Treatment agent No. | Structure of A1 | Modification amount [mmol/g] | g/d value | g/d rank |
|---|---|---|---|---|---|---|
| 2-1 | 2-1 | S1-2 | A1-22 | 0.125 | 1.1 | A |
| 2-2 | 2-2 | S1-14 | A1-22 | 0.138 | 1.0 | A |
| 2-3 | 2-3 | S1-37 | A1-22 | 0.187 | 1.0 | A |
| 2-4 | 2-4 | S1-43 | A1-22 | 0.156 | 1.1 | A |

TABLE 8A-continued

| Modified Example No. | Modified graphene No. | Treatment agent No. | Structure of A1 | Modification amount [mmol/g] | g/d value | g/d rank |
|---|---|---|---|---|---|---|
| 2-5 | 2-5 | S2-4 | A1-22 | 0.162 | 1.1 | A |
| 2-6 | 2-6 | S2-6 | A1-22 | 0.194 | 1.1 | A |
| 2-7 | 2-7 | S2-7 | A1-22 | 0.118 | 1.1 | A |
| 2-8 | 2-8 | S2-8 | A1-22 | 0.172 | 1.1 | A |
| 2-9 | 2-9 | S2-24 | A1-22 | 0.168 | 1.1 | A |
| 2-10 | 2-10 | S1-37 | A1-7 | 0.126 | 1.2 | A |
| 2-11 | 2-11 | S2-6 | A1-7 | 0.121 | 1.1 | A |
| 2-12 | 2-12 | S1-37 | A1-8 | 0.146 | 1.1 | A |
| 2-13 | 2-13 | S2-6 | A1-8 | 0.152 | 1.1 | A |
| 2-14 | 2-14 | S1-37 | A1-10 | 0.186 | 1.1 | A |
| 2-15 | 2-15 | S2-6 | A1-10 | 0.173 | 1.0 | A |
| 2-16 | 2-16 | S1-37 | A1-13 | 0.144 | 1.0 | A |
| 2-17 | 2-17 | S2-6 | A1-13 | 0.132 | 1.0 | A |
| 2-18 | 2-18 | S1-37 | A1-14 | 0.157 | 1.1 | A |
| 2-19 | 2-19 | S2-6 | A1-14 | 0.149 | 1.0 | A |
| 2-20 | 2-20 | S1-37 | A1-15 | 0.201 | 1.0 | A |
| 2-21 | 2-21 | S2-6 | A1-15 | 0.178 | 1.0 | A |
| 2-22 | 2-22 | S1-37 | A1-20 | 0.165 | 1.0 | A |
| 2-23 | 2-23 | S2-6 | A1-20 | 0.159 | 1.0 | A |
| 2-24 | 2-24 | S1-37 | A1-23 | 0.198 | 1.0 | A |
| 2-25 | 2-25 | S2-6 | A1-23 | 0.173 | 1.0 | A |
| 2-26 | 2-26 | S1-37 | A1-26 | 0.164 | 1.0 | A |
| 2-27 | 2-27 | S2-6 | A1-26 | 0.128 | 1.1 | A |
| 2-28 | 2-28 | S1-37 | A1-28 | 0.181 | 1.1 | A |
| 2-29 | 2-29 | S2-6 | A1-28 | 0.169 | 1.1 | A |
| 2-30 | 2-30 | S1-37 | A1-29 | 0.164 | 1.1 | A |
| 2-31 | 2-31 | S2-6 | A1-29 | 0.175 | 1.1 | A |
| 2-32 | 2-32 | S1-37 | A1-30 | 0.159 | 1.0 | A |
| 2-33 | 2-33 | S2-6 | A1-30 | 0.176 | 1.0 | A |
| 2-34 | 2-34 | S1-37 | A1-64 | 0.144 | 1.0 | A |
| 2-35 | 2-35 | S2-6 | A1-64 | 0.162 | 1.0 | A |
| 2-36 | 2-36 | S1-37 | A1-72 | 0.192 | 1.1 | A |
| 2-37 | 2-37 | S2-6 | A1-72 | 0.211 | 1.1 | A |
| 2-38 | 2-38 | S1-37 | A1-82 | 0.183 | 1.0 | A |
| 2-39 | 2-39 | S2-6 | A1-82 | 0.195 | 1.1 | A |
| 2-40 | 2-40 | S1-37 | A1-83 | 0.173 | 1.1 | A |
| 2-41 | 2-41 | S2-6 | A1-83 | 0.169 | 1.1 | A |
| 2-42 | 2-42 | S1-37 | A1-85 | 0.209 | 1.1 | A |
| 2-43 | 2-43 | S1-37 | A1-3 | 0.192 | 1.1 | A |
| 2-44 | 2-44 | S2-6 | A1-3 | 0.119 | 1.0 | A |
| 2-45 | 2-45 | S1-37 | A1-6 | 0.137 | 1.0 | A |
| 2-46 | 2-46 | S2-6 | A1-6 | 0.142 | 1.1 | A |
| 2-47 | 2-47 | S1-37 | A1-21 | 0.158 | 1.0 | A |
| 2-48 | 2-48 | S2-6 | A1-21 | 0.141 | 1.1 | A |

TABLE 8B

| Comparative Example No. | Comparative compound No. | Treatment agent | Modification amount [mmol/g] | g/d value | g/d rank |
|---|---|---|---|---|---|
| 2-1 | 2-1 | — | — | 0.8 | C |
| 2-2 | 2-2 | 4-Aminobenzoic acid | 0.171 | 0.9 | B |

(Method of Producing Resin Composite of Modified Graphene)

A resin sheet blended with any one of the modified graphenes produced in the foregoing was produced by using any one of Production Method 2-1, Production Method 2-2, and Production Method 2-3 described below. Further, the electroconductivity evaluation and thermal conductivity evaluation of the resultant sheet were performed.

In addition, a resin sheet blended with the graphene oxide (the comparative compound 2-1) and a resin sheet blended with the modified graphene (the comparative compound 2-2) produced by the production method described in Japanese Patent No. 3980637 were produced, and were subjected to the same evaluations.

Production Method 2-1, Production Method 2-2, or Production Method 2-3 is described below. Production Method 2-1 is a method relating to a sheet using a silicone resin, Production Method 2-2 is a method relating to a sheet using a urethane resin, and Production Method 2-3 is a method relating to a sheet using a polyimide.

[Production Method 2-1]

100 Parts of a vinyl-terminated polysiloxane DMS-V31 (weight-average molecular weight (Mw): 28,000, AZmax Co., Ltd.), 5 parts of a hydrogen-terminated polysiloxane HMS-301 (AZmax Co., Ltd.), and 60 parts of a modified graphene (or a comparative compound) were mixed with a spatula.

Next, the mixture was kneaded with a planetary mixer (NR-50, manufactured by Thinky Corporation) for 2 minutes, and was defoamed therewith for 1 minute. 0.8 Part of a platinum catalyst was added to the defoamed product, and was kneaded thereinto with a spatula. Next, the mixture was kneaded with a planetary mixer (NR-50, manufactured by Thinky Corporation) for 2 minutes, and was defoamed therewith for 1 minute. The resultant mixture was applied onto a metal plate with a bar coater, and was left at rest in a thermostatic chamber at 100° C. for 2 hours to be cured. Thus, the following silicone resin sheet was obtained:

Silicone resin sheet
 Thickness: 200±10 Lam
 The blending amount of the modified graphene (or the comparative compound): 20 vol % provided that the blending amount was calculated by defining the density of the modified graphene as 2.2 g/cm$^3$ and defining the density of any other material as 0.97 g/cm$^3$.

[Production Method 2-2]

100 Parts of a polyurethane UR-4800 serving as a binder resin (weight-average molecular weight (Mw): 4,800, Toyobo Co., Ltd.), 43 parts of a modified graphene (or a comparative compound), and an arbitrary amount of tetrahydrofuran (THF, manufactured by Kishida Chemical Co., Ltd.) were mixed, and the mixture was stirred for 1 hour while an ultrasonic wave was applied thereto. Thus, a dispersion liquid was prepared.

The resultant mixture was applied onto a metal plate with a bar coater, and was dried in a thermostatic dryer at 40° C. Next, the dried body was peeled from the metal plate, and was heated and pressurized with a small heat pressing machine (manufactured by AS ONE Corporation) at 150° C. and 0.5 kgf/m$^2$ for 3 minutes. Thus, the following urethane resin sheet was obtained:

Urethane resin sheet
 Thickness: 200±10 μm
 The blending amount of the modified graphene (or the comparative compound): 20 vol % provided that the blending amount was calculated by defining the density of the modified graphene as 2.2 g/cm$^3$ and defining the density of the urethane resin as 1.28 g/cm$^3$.

[Production Method 2-3]

100 Parts of a polyimide precursor U-VARNISH-S (solid content concentration: 20%, N-methylpyrrolidone content: 80%, Ube Industries, Ltd.) and 5.2 parts of a modified graphene (or a comparative compound) were mixed with a spatula.

Next, the mixture was kneaded with a planetary mixer (NR-50, manufactured by Thinky Corporation) for 2 minutes, and was defoamed therewith for 1 minute. The resultant mixture was applied onto a metal plate with a bar coater, and was left at rest in a thermostatic chamber at 100° C. for 2 hours so that its solvent was removed. Further, the residue was dried under a reduced pressure of 0.05 MPa in a vacuum dryer at 100° C. Further, the dried product was calcined in a muffle furnace at 290° C. for 30 minutes and at 350° C. for 30 minutes. Thus, the following polyimide sheet was obtained:

Polyimide sheet
Thickness: 85±3 μm
The blending amount of the modified graphene (or the comparative compound): 15 vol %
provided that the blending amount was calculated by defining the density of the modified graphene as 2.2 g/cm$^3$ and defining the density of the polyimide as 1.47 g/cm$^3$.

Examples 2-49 to 2-94

Modified graphene-blended silicone resin sheets were produced by: using the modified graphenes 2-1 to 2-46 shown in Table 8A; and using Production Method 2-1 described above. Further, the sheets were each cut into a predetermined sample shape, and were each subjected to an electroconductivity evaluation and a thermal conductivity evaluation. The results are shown in Table 9A.

Example 2-95 and Example 2-96

Modified graphene-blended urethane resin sheets were produced by: using the modified graphene 2-47 and the modified graphene 2-48 shown in Table 8A; and using Production Method 2-2 described above. Further, the sheets were each cut into a predetermined sample shape, and were each subjected to an electroconductivity evaluation and a thermal conductivity evaluation. The results are shown in Table 9A.

Example 2-97

A modified graphene-blended silicone resin sheet was produced by: using a vinyl-terminated polysiloxane DMS-V41 (weight-average molecular weight (Mw): 50,000, AZmax Co., Ltd.) instead of the vinyl-terminated polysiloxane DMS-V31; using the modified graphene 2-1; and using Production Method 2-1 described above. Further, the sheet was cut into a predetermined sample shape, and was subjected to an electroconductivity evaluation and a thermal conductivity evaluation. The results are shown in Table 9A.

Example 2-98

A modified graphene-blended silicone resin sheet was produced by: using a vinyl-terminated polysiloxane DMS-XX46 (weight-average molecular weight (Mw): 117,000, AZmax Co., Ltd.) instead of the vinyl-terminated polysiloxane DMS-XX31; using the modified graphene 2-2; and using Production Method 2-1 described above. Further, the sheet was cut into a predetermined sample shape, and was subjected to an electroconductivity evaluation and a thermal conductivity evaluation. The results are shown in Table 9A.

Example 2-99 and Example 2-100

Modified graphene-blended polyimide sheets were each produced by: using the modified graphene 2-24 or the modified graphene 2-25 shown in Table 8A; and using Production Method 2-3 described above. Further, the sheets were each cut into a predetermined sample shape, and were each subjected to a thermal conductivity evaluation. The results are shown in Table 10.

Comparative Examples

Compounds to be compared are described below.
Comparative compound 2-1: The graphene oxide (product name: GO, manufactured by New Metals and Chemicals Corporation, Ltd.)
Comparative compound 2-2: The graphene obtained in conformity with the production method described in Japanese Patent No. 3980637

Comparative Example 2-4

A graphene oxide-blended silicone resin sheet was produced by: using the comparative compound 2-1; and using Production Method 2-1 described above. Further, the sheet was cut into a predetermined sample shape, and was subjected to an electroconductivity evaluation and a thermal conductivity evaluation. The results are shown in Table 9B.

Comparative Example 2-5

A comparative compound 2-2-blended silicone resin sheet was produced by: using the comparative compound 2-2; and using Production Method 2-1 described above. Further, the sheet was cut into a predetermined sample shape, and was subjected to an electroconductivity evaluation and a thermal conductivity evaluation. The results are shown in Table 9B.

Comparative Example 2-6

A graphene oxide-blended silicone resin sheet was produced by: using the comparative compound 2-1; and using Production Method 2-3 described above. Further, the sheet was cut into a predetermined sample shape, and was subjected to a thermal conductivity evaluation. The results are shown in Table 10.

Comparative Example 2-7

A comparative compound 2-2-blended silicone resin sheet was produced by: using the comparative compound 2-2; and using Production Method 2-3 described above. Further, the sheet was cut into a predetermined sample shape, and was subjected to a thermal conductivity evaluation. The results are shown in Table 10.

(Evaluation)
[Electroconductivity Evaluation]
An electroconductivity evaluation was performed based on the surface electrical resistivity (kΩ/□) of each of the silicone resin sheet samples or the urethane resin sheets obtained in Examples and Comparative Examples. The surface electrical resistivity was measured in conformity with JIS K 7194 "Testing method for resistivity of conductive plastics with a four-point probe array," and the sample was classified into any one of a rank A to a rank C as described below by using the measured value. It has been generally known that the surface electrical resistivity of an electroconductive member is less than $1\times10^5$ Ω/□, and a member having a surface electrical resistivity of $1\times10^5$ Ω/□ or more is a static electricity diffusive member (lx $10^5$ Ω/□ or more and less than $1\times10^9$ Ω/□) or an antistatic member ($1\times10^9$ Ω/□ or more and less than $1\times10^{12}$ Ω/□). Accordingly, in one aspect of the present disclosure, only a resin sheet sample classified into a rank acceptable as an electroconductive member, that is, the rank A was defined as an acceptable rank.

[Evaluation Ranks]
Rank A . . . 10 kΩ/□≤surface electrical resistivity<100 kΩ/□
Rank B . . . 100 kΩ/□≤surface electrical resistivity<1,000 kΩ/□
Rank C . . . 1,000 kΩ/□≤surface electrical resistivity

[Thermal Conductivity Evaluation]

A thermal conductivity evaluation was performed based on the thermal conductivity of each of the silicone resin sheets, the urethane resin sheet samples, and the polyimide sheets (each having a thickness of 85±3 μm) obtained in Example 2-1 to Example 2-100 and Comparative Example 2-4 to Comparative Example 2-7 in its thickness direction.

First, the produced resin sheets were each cut into a size measuring 6 mm long by 11 mm wide. The sheet was used as a resin sheet sample, and its thermal diffusivity a in its thickness direction was measured with a temperature wave analyzer (manufactured by ULVAC-RIKO, Inc., FTC-1). The thermal conductivity λ of the sample was calculated from the equation "λ=α×Cp×ρ" by multiplying the thermal diffusivity a determined in the measurement by the specific heat Cp (weight fraction average) and density ρ (volume fraction average) thereof. The density was measured by using a submerged replacement method, and the specific heat was measured with a differential scanning calorimeter (PYRIS Diamond DSC-7, DSC, manufactured by PerkinElmer). The specific heat Cp and the density ρ needed for the calculation are as described below.

First, the silicone resin sheets and the urethane resin sheet samples obtained in Example 2-1 to Example 2-98, and Comparative Example 2-4 and Comparative Example 2-5 were classified into a rank A to a rank C as described below by using the values of their thermal conductivities. In the case of a general-purpose resin having imparted thereto thermal conductivity, a resin having a thermal conductivity of 1 W/m·K or more in its thickness direction is generally recognized as a high-performance heat conductive member. Accordingly, only a resin sheet sample classified into the rank A was defined as an acceptable rank.

[Evaluation Ranks]
Rank A . . . 1 W/m·K≤thermal conductivity
Rank B . . . 0.5 W/m·K≤thermal conductivity<1 W/m·K
Rank C . . . thermal conductivity<0.5 W/m·K

[Densities and Specific Heats of Respective Materials Used in Calculation]

The density ρ of each of the silicone resins: 0.97 g/cm³
The density ρ of the urethane resin: 1.28 g/cm³
The density ρ of each of the modified graphenes and the comparative compound 2-2: 2.2 g/cm³
The density ρ of the graphene oxide: 2.1 g/cm³
The specific heat Cp of each of the silicone resins: 1,600 J/kgK
The specific heat Cp of the urethane resin: 1,900 J/kgK
The specific heat Cp of each of the modified graphenes and the comparative compound 2-2: 710 J/kgK
The specific heat Cp of the graphene oxide: 700 J/kgK
The results are shown in Tables 9A and 9B.

Further, the polyimide sheet obtained in Example 2-99, Example 2-100, Comparative Example 2-6, or Comparative Example 2-7 was classified into any one of a rank A to a rank C as described below by using the value of its thermal conductivity. Only a sheet sample classified into the rank A was defined as an acceptable rank. Unlike the above-mentioned general-purpose resin sheet, there is no general thermal conductivity criterion for an engineering plastic-based resin.

[Evaluation Ranks]
Rank A . . . 0.6 W/m·K≤thermal conductivity
Rank B . . . 0.3 W/m·K≤thermal conductivity<0.6 W/m·K
Rank C . . . thermal conductivity<0.3 W/m·K

[Densities and Specific Heats of Respective Materials Used in Calculation]

The density ρ of the polyimide: 1.47 g/cm³
The density ρ of each of the modified graphenes and the comparative compound 2-2: 2.2 g/cm³
The density ρ of the graphene oxide: 2.1 g/cm³
The specific heat Cp of the polyimide resin: 1,130 J/kgK
The specific heat Cp of each of the modified graphenes and the comparative compound 2-2: 710 J/kgK
The specific heat Cp of the graphene oxide: 700 J/kgK
The results are shown in Table 10.

TABLE 9A

| Example | Production method | Filler (Modified graphene No.) | Weight-average molecular weight of resin | Filler amount (vol %) | Surface electrical resistivity (KΩ/□) | Resistivity rank | Thermal conductivity (W/m · K) | Thermal conductivity rank |
|---|---|---|---|---|---|---|---|---|
| 2-49 | 2-1 | 2-1 | 28,000 | 20 | 55 | A | 1.3 | A |
| 2-50 | 2-1 | 2-2 | 28,000 | 20 | 45 | A | 1.6 | A |
| 2-51 | 2-1 | 2-3 | 28,000 | 20 | 32 | A | 1.7 | A |
| 2-52 | 2-1 | 2-4 | 28,000 | 20 | 41 | A | 1.5 | A |
| 2-53 | 2-1 | 2-5 | 28,000 | 20 | 43 | A | 1.3 | A |
| 2-54 | 2-1 | 2-6 | 28,000 | 20 | 35 | A | 1.7 | A |
| 2-55 | 2-1 | 2-7 | 28,000 | 20 | 53 | A | 1.3 | A |
| 2-56 | 2-1 | 2-8 | 28,000 | 20 | 23 | A | 1.4 | A |
| 2-57 | 2-1 | 2-9 | 28,000 | 20 | 46 | A | 1.5 | A |
| 2-58 | 2-1 | 2-10 | 28,000 | 20 | 37 | A | 1.4 | A |
| 2-59 | 2-1 | 2-11 | 28,000 | 20 | 22 | A | 1.4 | A |
| 2-60 | 2-1 | 2-12 | 28,000 | 20 | 47 | A | 1.3 | A |
| 2-61 | 2-1 | 2-13 | 28,000 | 20 | 36 | A | 1.6 | A |
| 2-62 | 2-1 | 2-14 | 28,000 | 20 | 38 | A | 1.6 | A |
| 2-63 | 2-1 | 2-15 | 28,000 | 20 | 28 | A | 1.4 | A |
| 2-64 | 2-1 | 2-16 | 28,000 | 20 | 30 | A | 1.6 | A |
| 2-65 | 2-1 | 2-17 | 28,000 | 20 | 27 | A | 1.3 | A |
| 2-66 | 2-1 | 2-18 | 28,000 | 20 | 43 | A | 1.7 | A |
| 2-67 | 2-1 | 2-19 | 28,000 | 20 | 29 | A | 1.3 | A |
| 2-68 | 2-1 | 2-20 | 28,000 | 20 | 37 | A | 1.5 | A |
| 2-69 | 2-1 | 2-21 | 28,000 | 20 | 57 | A | 1.5 | A |
| 2-70 | 2-1 | 2-22 | 28,000 | 20 | 35 | A | 1.4 | A |

TABLE 9A-continued

| Example | Production method | Filler (Modified graphene No.) | Weight-average molecular weight of resin | Filler amount (vol %) | Surface electrical resistivity (KΩ/□) | Resistivity rank | Thermal conductivity (W/m · K) | Thermal conductivity rank |
|---|---|---|---|---|---|---|---|---|
| 2-71 | 2-1 | 2-23 | 28,000 | 20 | 55 | A | 1.3 | A |
| 2-72 | 2-1 | 2-24 | 28,000 | 20 | 36 | A | 1.4 | A |
| 2-73 | 2-1 | 2-25 | 28,000 | 20 | 43 | A | 1.3 | A |
| 2-74 | 2-1 | 2-26 | 28,000 | 20 | 44 | A | 1.5 | A |
| 2-75 | 2-1 | 2-27 | 28,000 | 20 | 56 | A | 1.3 | A |
| 2-76 | 2-1 | 2-28 | 28,000 | 20 | 20 | A | 1.6 | A |
| 2-77 | 2-1 | 2-29 | 28,000 | 20 | 17 | A | 1.8 | A |
| 2-78 | 2-1 | 2-30 | 28,000 | 20 | 48 | A | 1.7 | A |
| 2-79 | 2-1 | 2-31 | 28,000 | 20 | 35 | A | 1.5 | A |
| 2-80 | 2-1 | 2-32 | 28,000 | 20 | 33 | A | 1.3 | A |
| 2-81 | 2-1 | 2-33 | 28,000 | 20 | 64 | A | 1.5 | A |
| 2-82 | 2-2 | 2-34 | 28,000 | 20 | 71 | A | 1.4 | A |
| 2-83 | 2-3 | 2-35 | 28,000 | 20 | 63 | A | 1.3 | A |
| 2-84 | 2-4 | 2-36 | 28,000 | 20 | 19 | A | 1.3 | A |
| 2-85 | 2-5 | 2-37 | 28,000 | 20 | 32 | A | 1.3 | A |
| 2-86 | 2-6 | 2-38 | 28,000 | 20 | 47 | A | 1.5 | A |
| 2-87 | 2-7 | 2-39 | 28,000 | 20 | 62 | A | 1.6 | A |
| 2-88 | 2-8 | 2-40 | 28,000 | 20 | 47 | A | 1.3 | A |
| 2-89 | 2-9 | 2-41 | 28,000 | 20 | 28 | A | 1.4 | A |
| 2-90 | 2-10 | 2-42 | 28,000 | 20 | 46 | A | 1.5 | A |
| 2-91 | 2-11 | 2-43 | 28,000 | 20 | 72 | A | 1.4 | A |
| 2-92 | 2-12 | 2-44 | 28,000 | 20 | 56 | A | 1.3 | A |
| 2-93 | 2-13 | 2-45 | 28,000 | 20 | 74 | A | 1.4 | A |
| 2-94 | 2-14 | 2-46 | 28,000 | 20 | 48 | A | 1.6 | A |
| 2-95 | 2-2 | 2-47 | 28,000 | 20 | 27 | A | 1.3 | A |
| 2-96 | 2-2 | 2-48 | 28,000 | 20 | 49 | A | 1.3 | A |
| 2-97 | 2-1 | 2-1 | 50,000 | 20 | 85 | A | 1.1 | A |
| 2-98 | 2-1 | 2-2 | 117,000 | 20 | 97 | A | 1.0 | A |

TABLE 9B

| Comparative Example | Production method | Filler (Modified graphene No.) | Weight-average molecular weight of resin | Filler amount (vol %) | Surface electrical resistivity (KΩ/□) | Resistivity rank | Thermal conductivity (W/m · K) | Thermal conductivity rank |
|---|---|---|---|---|---|---|---|---|
| 2-4 | 2-1 | Comparative compound 2-1 | 28,000 | 20 | 3,247 | C | 0.3 | C |
| 2-5 | 2-1 | Comparative compound 2-2 | 28,000 | 20 | 112 | B | 0.7 | B |

TABLE 10

| | Production method | Filler (Modified graphene No.) | Filler amount (vol %) | Thermal conductivity (W/m · K) | Thermal conductivity rank |
|---|---|---|---|---|---|
| Example 2-99 | 2-3 | 2-24 | 15 | 1.0 | A |
| Example 2-100 | 2-3 | 2-25 | 15 | 0.8 | A |
| Comparative Example 2-6 | 2-3 | Comparative compound 2-1 | 15 | 0.3 | C |
| Comparative Example 2-7 | 2-3 | Comparative compound 2-2 | 15 | 0.5 | B |

<Production of Modified Graphene Dispersion>

A modified graphene dispersion according to one aspect of the present disclosure and a comparative graphene dispersion were each produced by a method described below.

Example 2-201: Modified Graphene Dispersion Production Example 2-201

100 Parts of the modified graphene 2-20, 350 parts of toluene, 350 parts of ethyl acetate, and 300 parts of 2-butanone serving as dispersion media, and 750 parts of glass beads (each having a diameter of 1 mm) were mixed, and the mixture was subjected to dispersion with an attritor [manufactured by Nippon Coke & Engineering Co., Ltd.] for 3 hours. After that, the resultant was filtered with a mesh to provide each modified graphene dispersion according to one aspect of the present disclosure.

Examples 2-202 to 2-208: Modified Graphene Dispersion Production Examples 2-202 to 2-208

Modified graphene dispersions were each obtained by the same operation as that of Graphene Dispersion Production Example 2-201 except that the modified graphene 2-20 was changed to any one of modified graphenes shown in Table 11.

Comparative Examples 2-201 to 2-203:
Comparative Graphene Dispersion Production Examples 2-201 to 2-203

Comparative graphene dispersions were each obtained by the same operation as that of Graphene Dispersion Production Example 2-201 except that the modified graphene 2-20 was changed to any one of comparative compounds 2-1 to 2-3 shown in Table 11.

<Evaluation>
<Sample Production>

Each of the modified graphene dispersions and the comparative graphene dispersions was applied onto a PET film by a bar coating method (number of the annealing wire of a bar coater: No. 10), and was dried under reduced pressure overnight. Thus, samples were produced. The resultant sample was evaluated by using the above-mentioned electroconductivity evaluation method.

The results are shown in Table 11.

TABLE 11

|  |  | Modified graphene/ comparative compound | Surface electrical resistivity (kΩ/□) | Resistivity rank |
|---|---|---|---|---|
| Example | 2-201 | Modified graphene 2-20 | 55 | A |
|  | 2-202 | Modified graphene 2-36 | 62 | A |
|  | 2-203 | Modified graphene 2-15 | 78 | A |
|  | 2-204 | Modified graphene 2-17 | 70 | A |
|  | 2-205 | Modified graphene 2-19 | 72 | A |
|  | 2-206 | Modified graphene 2-43 | 66 | A |
|  | 2-207 | Modified graphene 2-4 | 68 | A |
|  | 2-208 | Modified graphene 2-24 | 61 | A |
| Comparative Example | 2-201 | Comparative compound 2-1 | 4,276 | C |
|  | 2-202 | Comparative compound 2-2 | 329 | B |
|  | 2-203 | Comparative compound 2-3 | 107 | B |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-034913, filed Feb. 27, 2019, Japanese Patent Application No. 2019-034911, filed Feb. 27, 2019, and Japanese Patent Application No. 2020-021921, filed Feb. 12, 2020, which are hereby incorporated by reference herein in their entirety.

What is claimed is:

1. A modified graphene having a structure represented by formula (I), wherein the modified graphene has a ratio (g/d) of an intensity "g" of a G band to an intensity "d" of a D band of 1.0 to 2.0 in a Raman spectroscopy spectrum thereof:

$$Gr1\text{-}Ar1\text{-}X1\text{-}(Y1)_{n1} \quad (I)$$

wherein, in the formula (I):

Gr1 represents a single-layer graphene or a multilayer graphene,

Ar1 represents an arylene group having 6 to 18 carbon atoms,

X1 represents:
  a single bond,
  a linear, branched, or cyclic alkylene group having 1 to 20 carbon atoms, or
  a group obtained by substituting at least one carbon atom in a linear, branched, or cyclic alkylene group having 1 to 20 carbon atoms with at least one structure selected from the group consisting of —O—, —NH—,

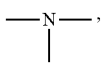

—CO—, —COO—, —CONH—, and an arylene group,

Y1 represents:
  when the X1 represents a single bond, an atom or a group bonded to at least one carbon atom of the Ar1,
  when the X1 represents a linear, branched, or cyclic alkylene group having 1 to 20 carbon atoms, an atom or a group bonded to a carbon atom in the alkylene group, or
  when the X1 represents a group obtained by substituting at least one carbon atom in a linear, branched, or cyclic alkylene group having 1 to 20 carbon atoms with at least one structure selected from the group consisting of —O—, —NH—,

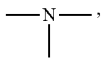

—CO—, —COO—, —CONH—, and an arylene group, an atom or a group bonded to a carbon atom in the group, and the Y1 represents at least one atom or group selected from the group consisting of:
  a hydrogen atom, a fluorine atom, a chlorine atom, a bromine atom, and an iodine atom,
  a fluoroalkyl group having 1 to 6 carbon atoms,
  a cyano group, a nitro group, an acyl group, an amide group, a vinyl group, a carboxylic acid group, a carboxylic acid ester group, and a phosphoric acid group,
  an alkylsilyl group having 3 to 6 carbon atoms,
  an alkylsilyl ether group having 3 to 6 carbon atoms, and
  a siloxane group, and n1 represents an integer of 1 or more, and when the n1 is 2 or more, the Y1s may represent groups identical to each other or groups different from each other.

2. The modified graphene according to claim 1, wherein in the formula (I), the Ar1 represents a phenylene group, a biphenylene group, a triphenylene group, or a naphthalene group, the X1 represents a single bond, the Y1 represents a carboxylic acid group, and the n1 is from 1 to 6.

3. The modified graphene according to claim 1, wherein in the formula (I), the Ar1 represents a phenylene group, the X1 represents a group obtained by substituting at least one carbon atom in a branched alkylene group having 1 to 20 carbon atoms with

or —CONH—, the Y1 represents a phosphoric acid group, and the n1 is from 1 to 4.

4. The modified graphene according to claim 1, wherein in the formula (I), the Ar1 represents a phenylene group, the X1 represents a single bond, the Y1 represents a nitro group, and the n1 is from 1 to 3.

5. The modified graphene according to claim 1, wherein in the formula (I), the Ar1 represents a phenylene group, the X1 represents a group obtained by substituting at least one carbon atom in a branched alkylene group having 1 to 20 carbon atoms with

—CO—, or —CONH—, the Y1 represents a hydrogen atom or a vinyl group, and the n1 is from 1 to 3.

6. The modified graphene according to claim 1, wherein a siloxane group in the formula (I) is at least one selected from the group consisting of formulae (II) to (IV):

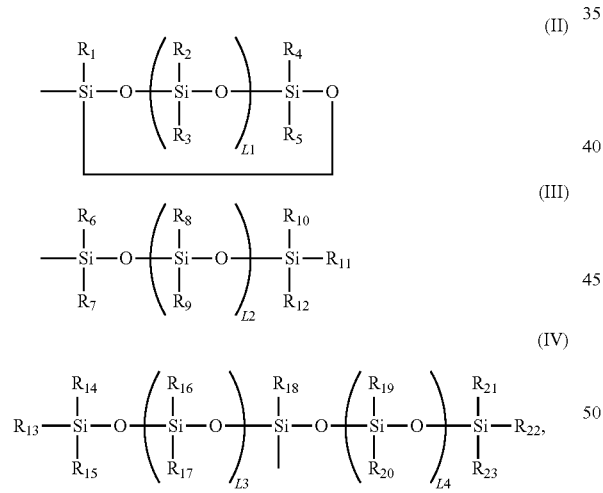

wherein, in the formulae (II) to (IV), $R_1$ to $R_{23}$ each independently represent an alkyl group, an amino group, a vinyl group, an acrylic group, a carboxylic acid ester group, a carboxylic acid group, a hydroxy group, or an aryl group, L1 represents an integer from 1 to 6, and L2 and (L3+L4) each represent a number from 0 to 650.

7. The modified graphene according to claim 1, wherein when the Y1 in the formula (I) represents a group, a number of moles of the group with respect to 1 g of the modified graphene is 0.10 mmol or more.

8. The modified graphene according to claim 7, wherein when the Y1 in the formula (I) represents a group, the number of moles of the group with respect to 1 g of the modified graphene is 0.10 mmol to 1.20 mmol.

9. A modified graphene-resin composite comprising:
the modified graphene of claim 1; and
a resin.

10. A modified graphene dispersion comprising:
the modified graphene of claim 1; and
water or an organic solvent.

11. The modified graphene according to claim 1, which has the ratio (g/d) of 1.1 to 2.0.

12. A modified graphene having a structure represented by formula (I), wherein the modified graphene has a ratio (g/d) of an intensity "g" of a G band to an intensity "d" of a D band of 1.0 or more in a Raman spectroscopy spectrum thereof:

Gr1-Ar1-X1-(Y1)$_{n1}$  (I)

wherein, in the formula (I):
Gr1 represents a single-layer graphene or a multilayer graphene,
Ar1 represents at least one selected from the group consisting of a phenylene group, a biphenylene group, a triphenylene group, and a naphthalene group,
X1 represents a single bond,
Y1 represents a carboxylic acid group,
n1 represents an integer of 1 or more, and when the n1 is 2 or more, the Y1s may represent groups identical to each other or groups different from each other, and
-Ar1-X1-(Y1)$_{n1}$ is at least one selected from the group consisting of formulae A1-23, A1-24, A1-25, A1-32, A1-45, A1-60, A1-63, A1-64, and A1-67:

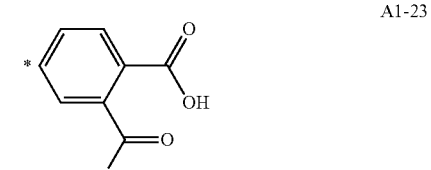

A1-23

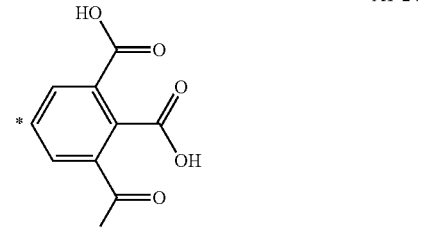

A1-24

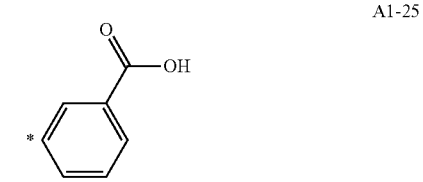

A1-25

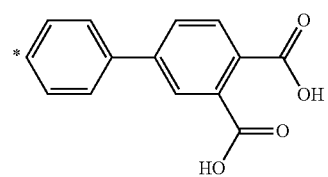

A1-32

A1-45
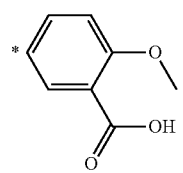
A1-60
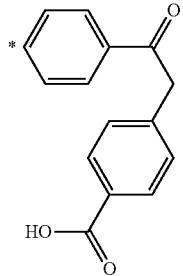
A1-63
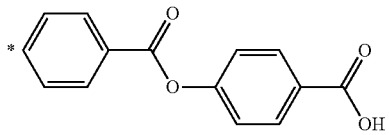
A1-64
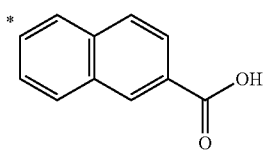
A1-67
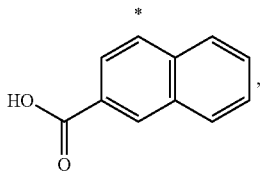
where * represents a bonding site with a carbon atom forming the Gr1.
* * * * *